(12) United States Patent
Scadden et al.

(10) Patent No.: US 10,961,308 B2
(45) Date of Patent: Mar. 30, 2021

(54) EMBIGIN INHIBITION FOR PROMOTION OF HEMATOPOIETIC STEM AND PROGENITOR CELL EXPANSION

(71) Applicants: THE GENERAL HOSPITAL CORPORATION, Boston, MA (US); PRESIDENT AND FELLOWS OF HARVARD COLLEGE, Cambridge, MA (US)

(72) Inventors: David T. Scadden, Weston, MA (US); Lev Silberstein, Brookline, MA (US); Peter Kharchenko, Brookline, MA (US)

(73) Assignees: THE GENERAL HOSPITAL CORPORATION, Boston, MA (US); PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 47 days.

(21) Appl. No.: 15/740,619

(22) PCT Filed: Jun. 29, 2016

(86) PCT No.: PCT/US2016/039969
§ 371 (c)(1),
(2) Date: Dec. 28, 2017

(87) PCT Pub. No.: WO2017/004127
PCT Pub. Date: Jan. 5, 2017

(65) Prior Publication Data
US 2018/0186879 A1 Jul. 5, 2018

Related U.S. Application Data

(60) Provisional application No. 62/186,075, filed on Jun. 29, 2015.

(51) Int. Cl.
| | |
|---|---|
| *C07K 16/28* | (2006.01) |
| *A61K 35/14* | (2015.01) |
| *A61K 35/28* | (2015.01) |
| *A61K 35/50* | (2015.01) |
| *A61K 39/395* | (2006.01) |
| *C12N 5/0789* | (2010.01) |
| *A61K 9/00* | (2006.01) |
| *A61K 35/51* | (2015.01) |
| *A61K 45/06* | (2006.01) |
| *A61K 39/00* | (2006.01) |

(52) U.S. Cl.
CPC ........ *C07K 16/2803* (2013.01); *A61K 9/0019* (2013.01); *A61K 35/14* (2013.01); *A61K 35/28* (2013.01); *A61K 35/50* (2013.01); *A61K 35/51* (2013.01); *A61K 39/395* (2013.01); *A61K 45/06* (2013.01); *C12N 5/0647* (2013.01); *A61K 2039/505* (2013.01); *C07K 2317/21* (2013.01); *C07K 2317/24* (2013.01); *C07K 2317/74* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 8,858,944 B2 | 10/2014 | Kino et al. | |
| 2013/0121914 A1* | 5/2013 | Kino ................ | A61P 37/08 424/1.49 |

FOREIGN PATENT DOCUMENTS

| | | |
|---|---|---|
| WO | 2006019357 A1 | 2/2006 |
| WO | 2014/110560 A1 | 7/2014 |

OTHER PUBLICATIONS

Appelbaum "Haematopoietic cell transplantation as immunotherapy." Nature 411.6835 (2001): 385-389 (Year: 2001).*
Silberstein et al., "Embigin Regulates HSPC Homing and Quiescence and Acts as a Cell Surface Marker for a Niche Factor-Enriched Subset of Osteolineage Cells", Blood 126(23):663 (2015).
Bourdeau et al.,"Inhibition of T Cell Protein Tyrosine Phosphatase Enhances Interleukin-18-Dependent Hematopoietic Stem Cell Expansion", Stem Cells, 31, 293-304, (2013).
Gerber et al., "The role of VEGF in normal and neoplastic hematopoiesis", J. Mol. Med., 81,(1),20-31, (2003).
Min et al., "Paradoxical effects of interleukin-18 on the severity of acute graft-versus-host disease mediated by CD4+ and CD8+ T-cell subsets after experimental allogeneic bone marrow transplantation", Blood, 104, (10), 3393-3399, (2004).
Pelloso et al., "Immunological consequences of interleukin 12 administration after autologous stem cell transplantation", Clin Cancer Res, 10, (6), 1935-1942, (2004).
Pridans et al., "Identification of Pax5 target genes in early B cell differentiation", The Journal of Immunology, 180, (3), 1719-1728, (2008).
Shaiegan et al., "Effect of IL-18 and sIL2R on aGVHD occurrence after hematopoietic stem cell transplantation in some Iranian patients", Transpl Immunol., 15, (3), 223-227, (2006).
Yang et al., "Identification of Lin-Sca1+ kit+ CD34+ Flt3-short-term hematopoietic stem cells capable of rapidly reconstituting and rescuing myeloablated transplant recipients", Blood, 105, (7), 2717-2723, (2005).

* cited by examiner

*Primary Examiner* — Emily A Cordas
(74) *Attorney, Agent, or Firm* — Nixon Peabody LLP; David S. Resnick; Shayne Y. Huff

(57) ABSTRACT

Disclosed herein are methods for enhancing hematopoietic reconstitution of a subject. One method involves administering a therapeutically effective amount of an inhibitor of Embigin to a recipient subject and can also optionally include administering hematopoietic stem/progenitor cells to the subject. Another method involves administering an inhibitor of Embigin to a donor prior to harvest of hematopoietic stem/progenitor cells. Pharmaceutical compositions relating to the methods are also described.

14 Claims, 24 Drawing Sheets

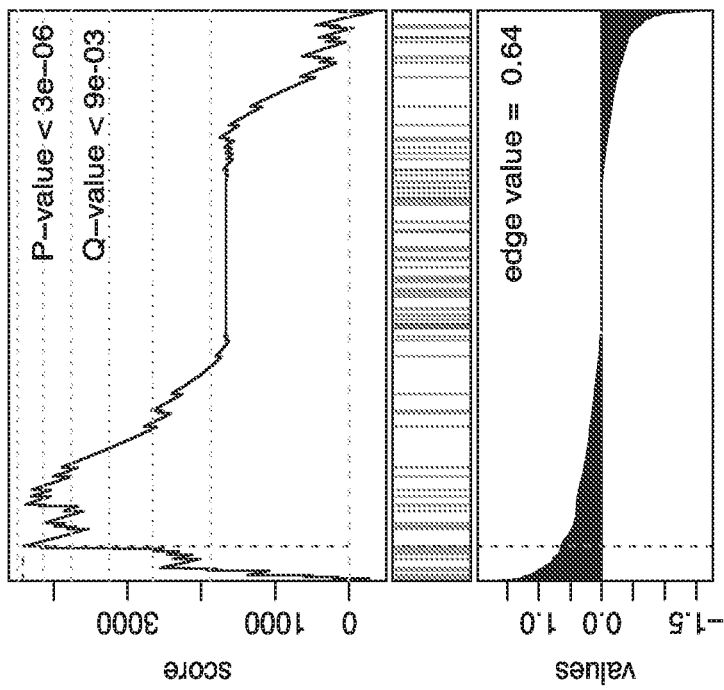
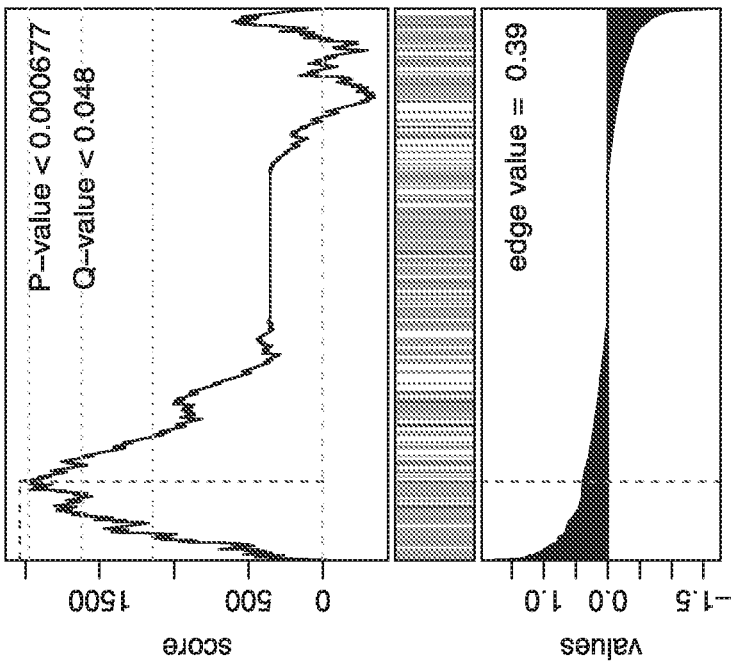
Fig. 4

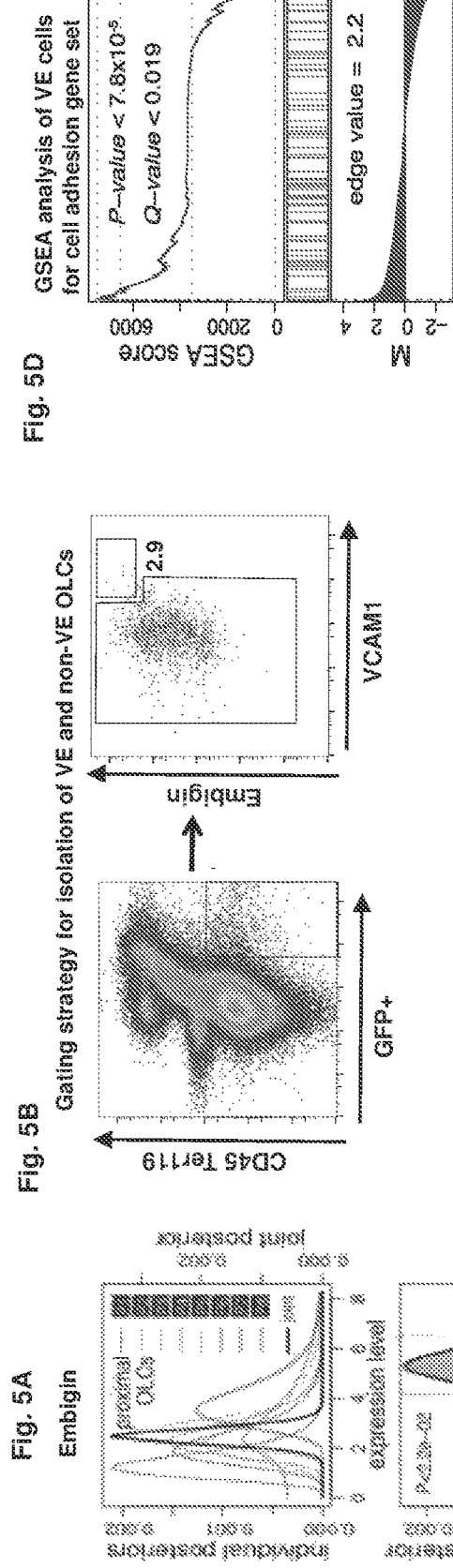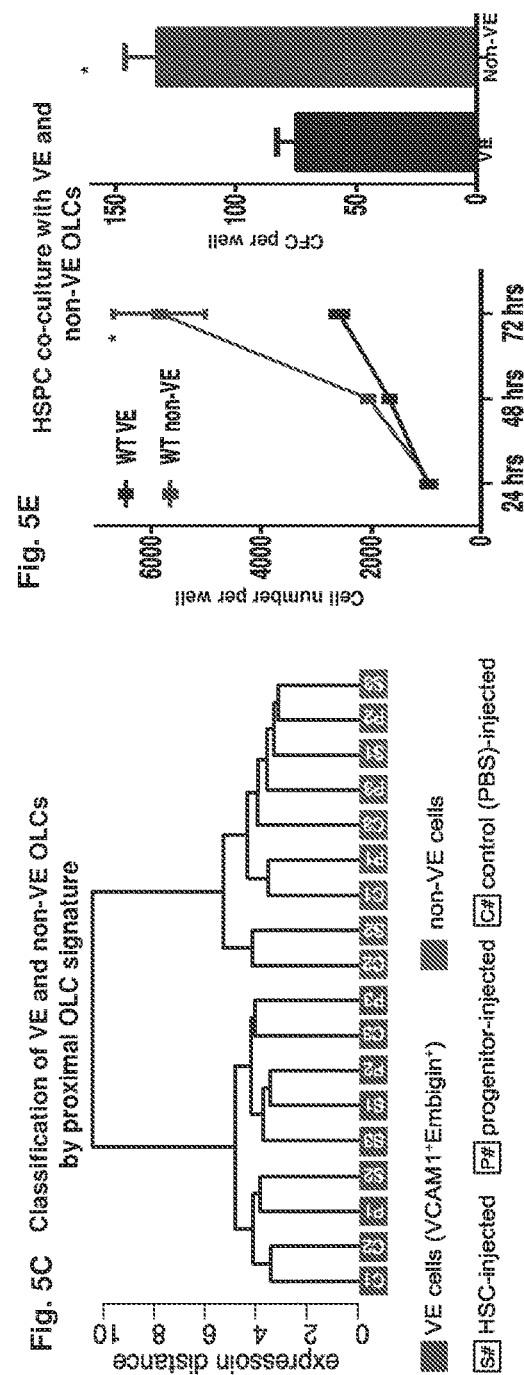

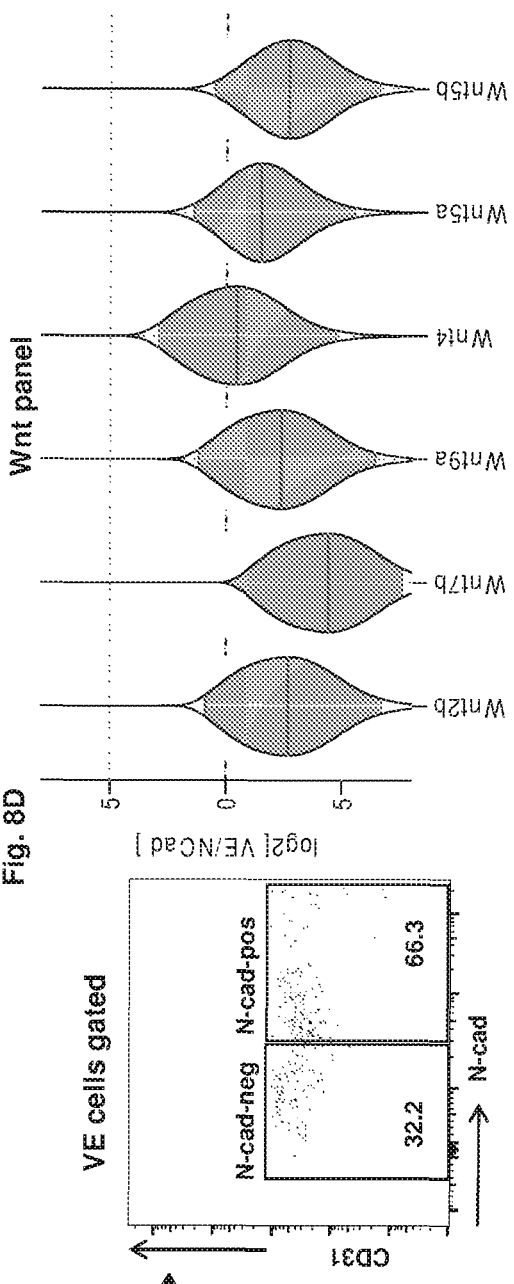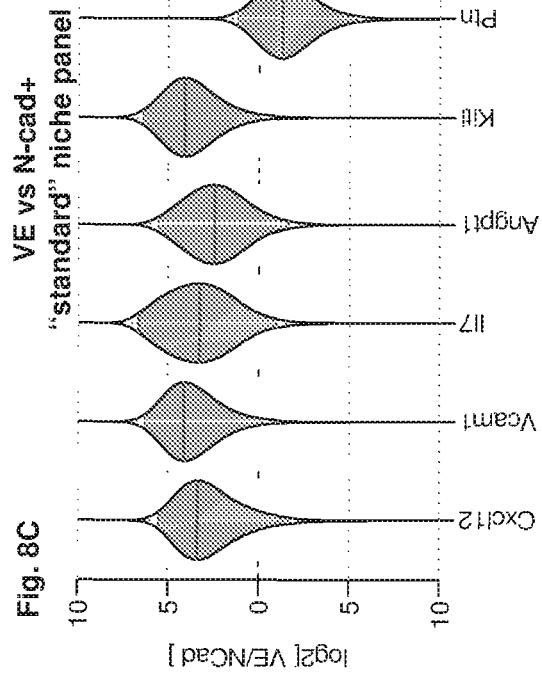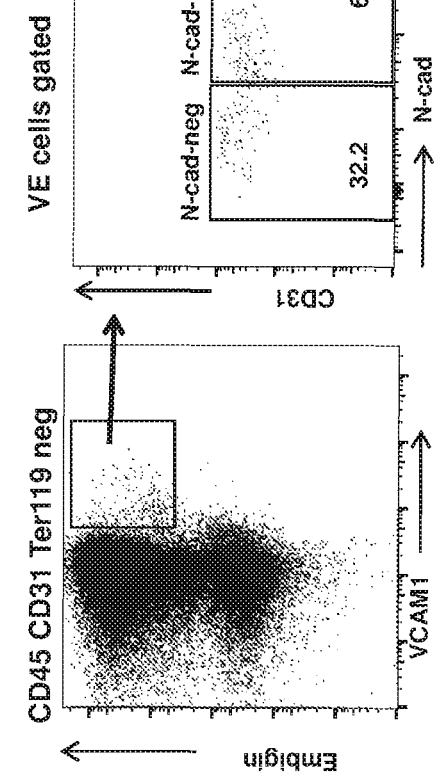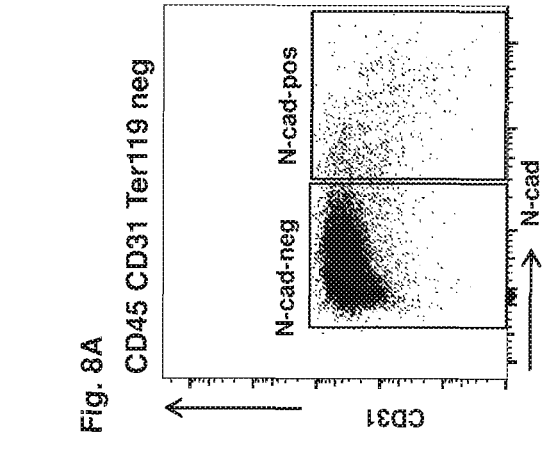

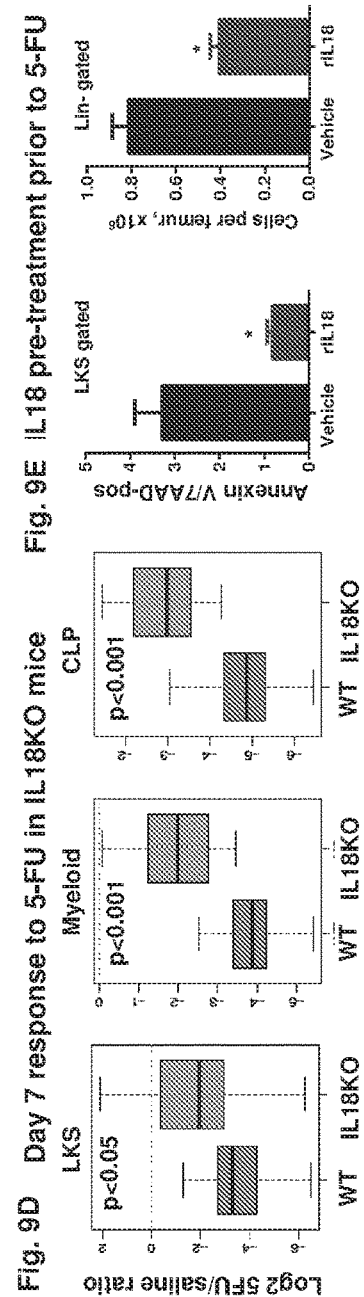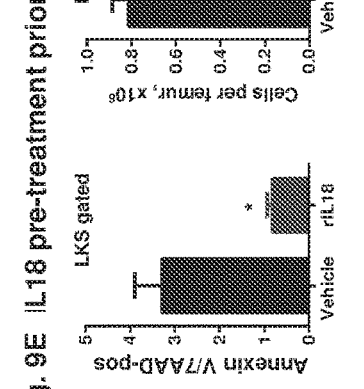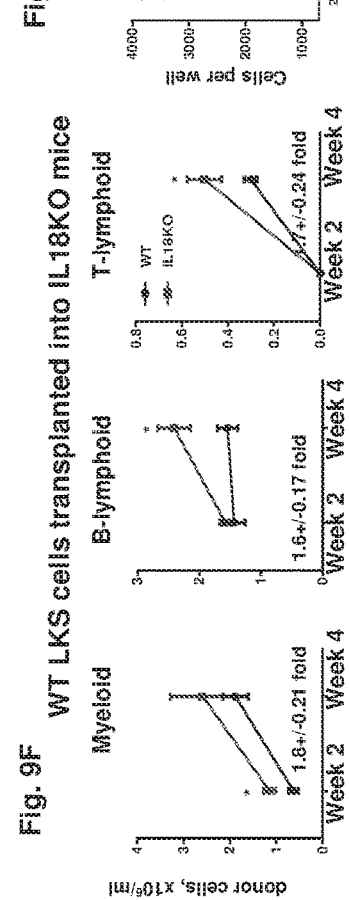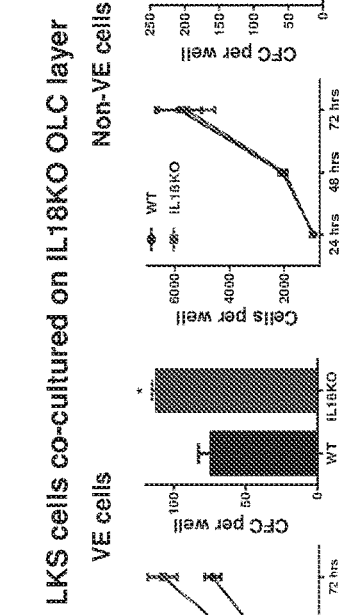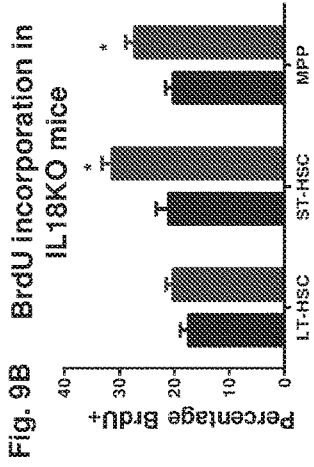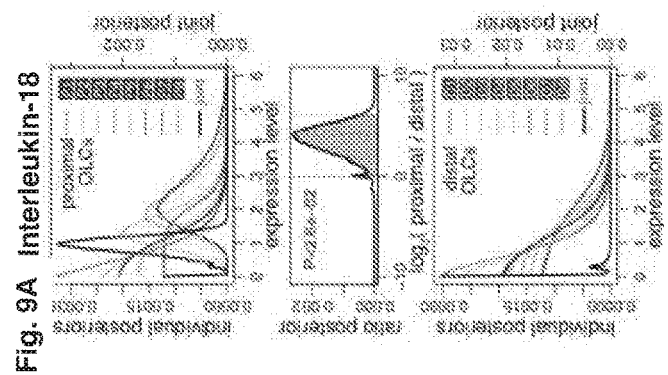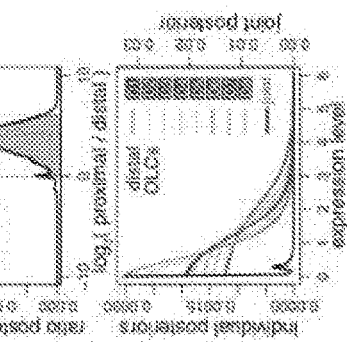

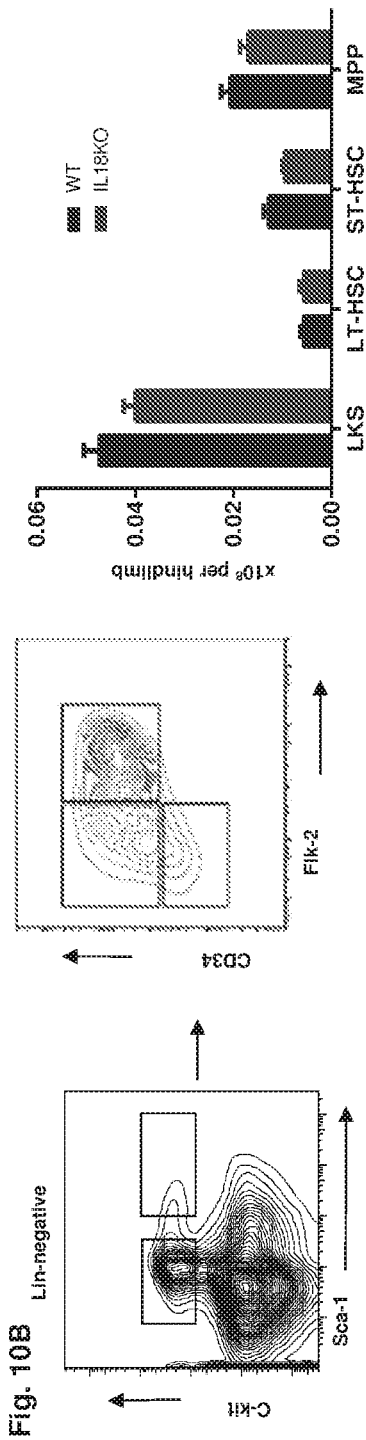
Fig. 10A
Fig. 10B
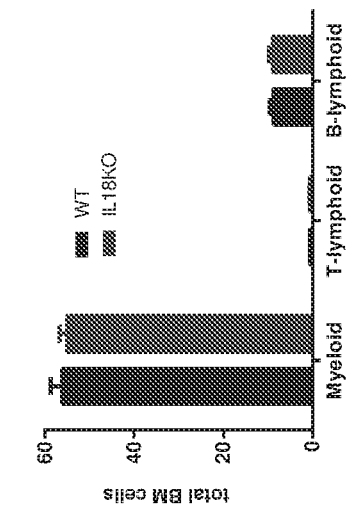
Fig. 10C

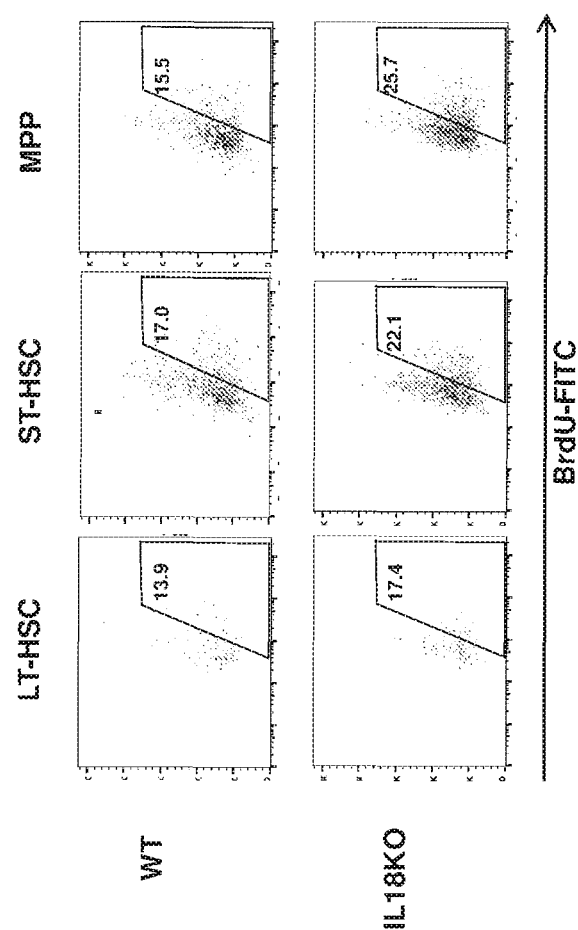

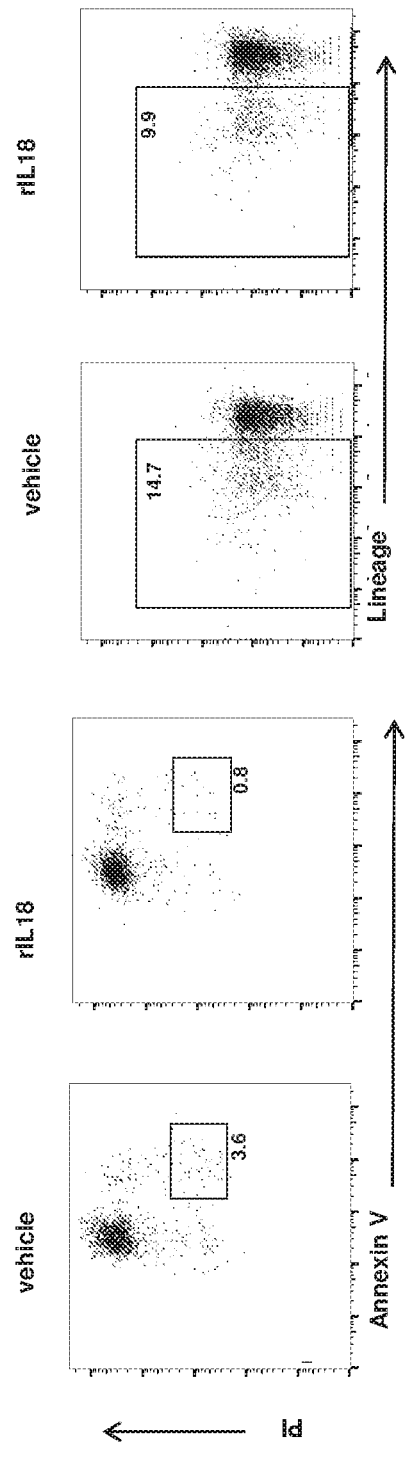

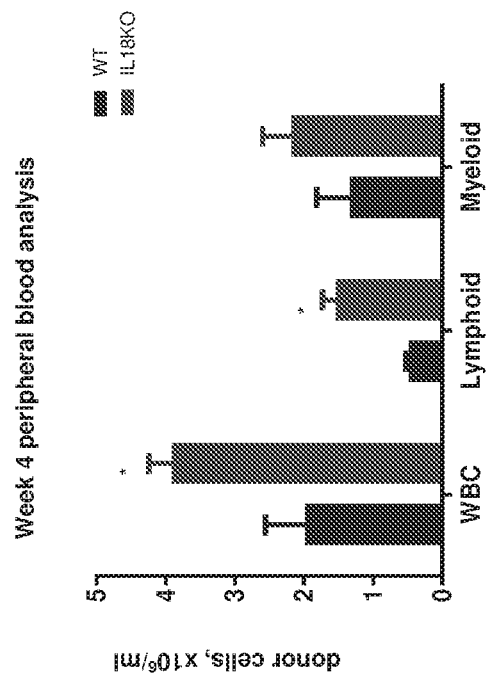
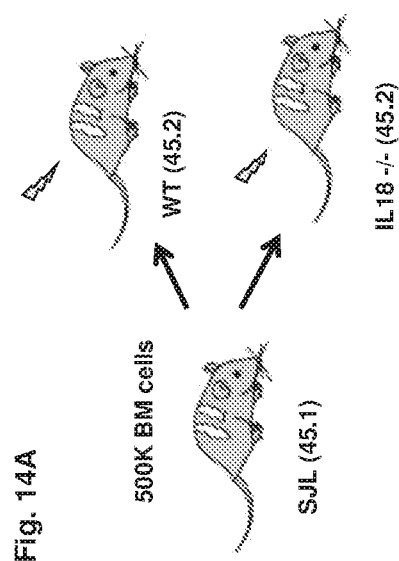
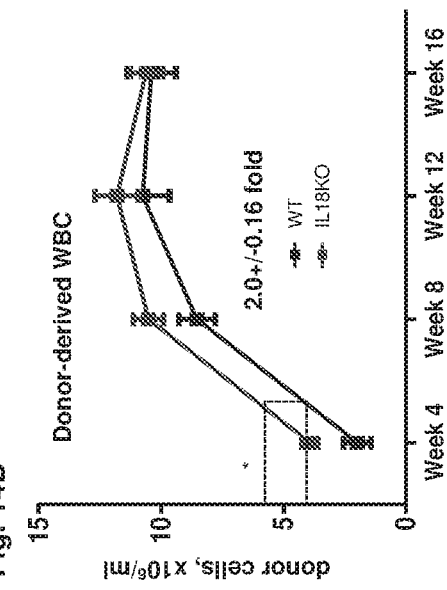

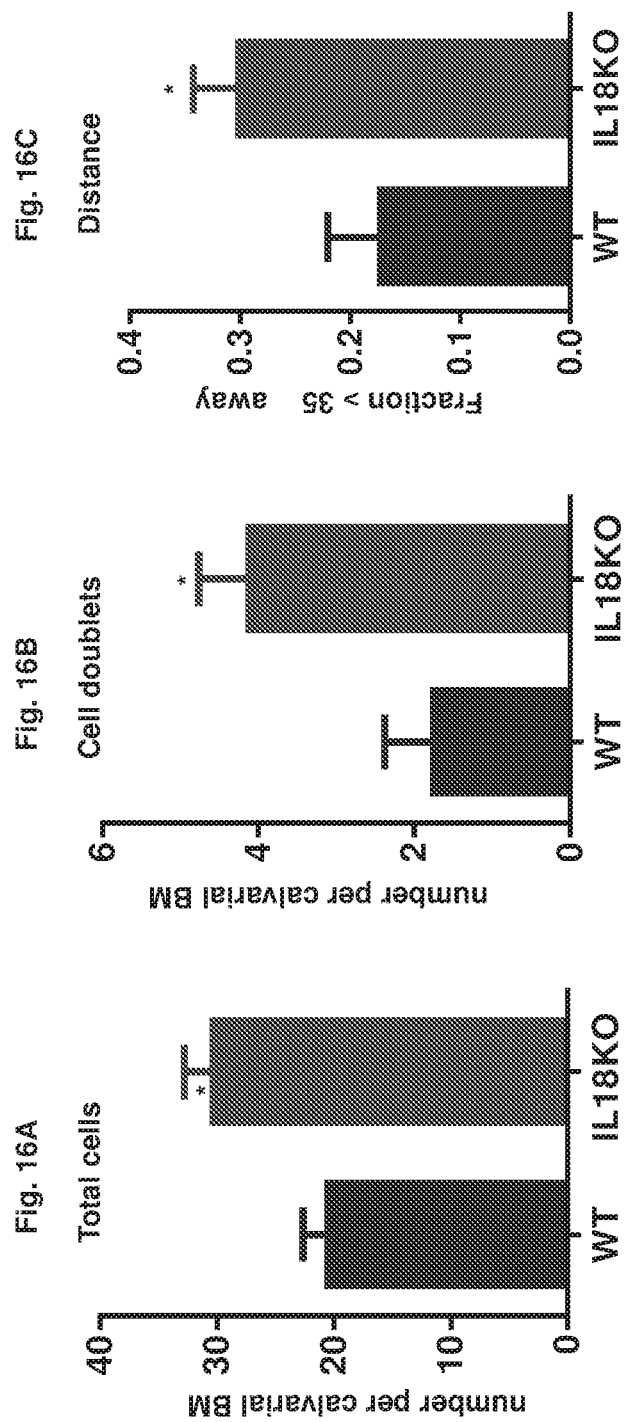

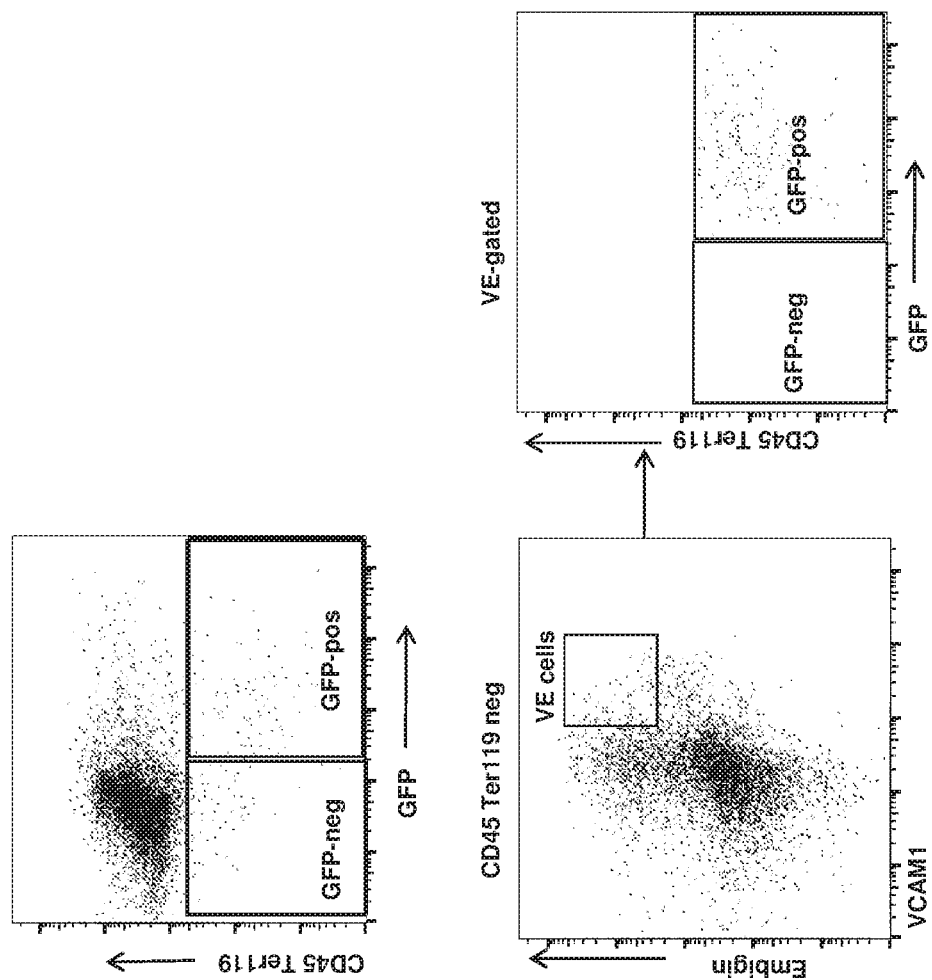

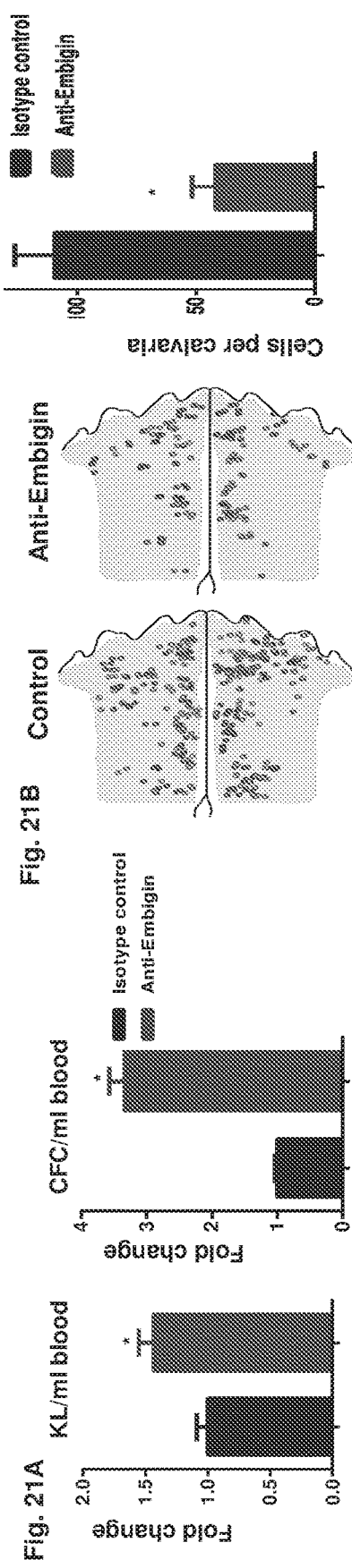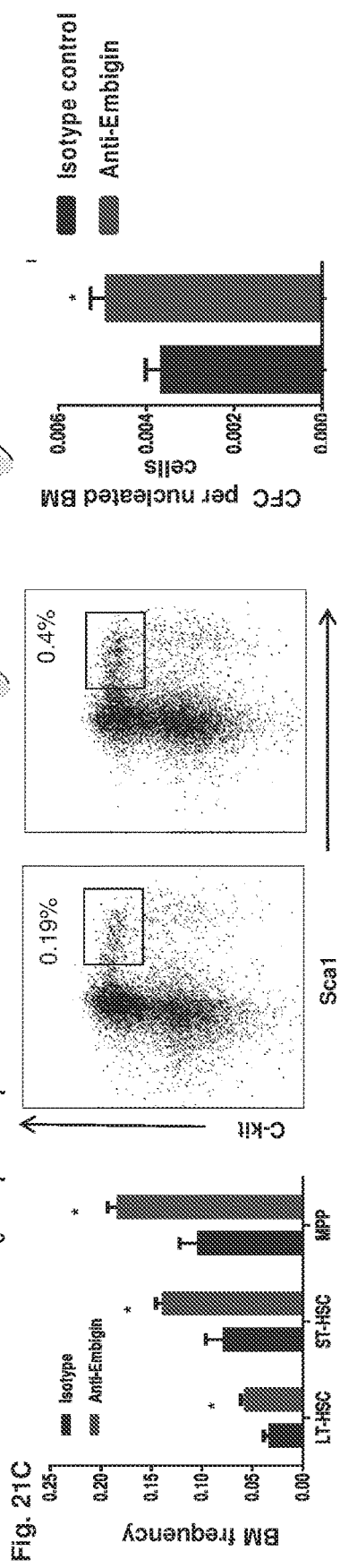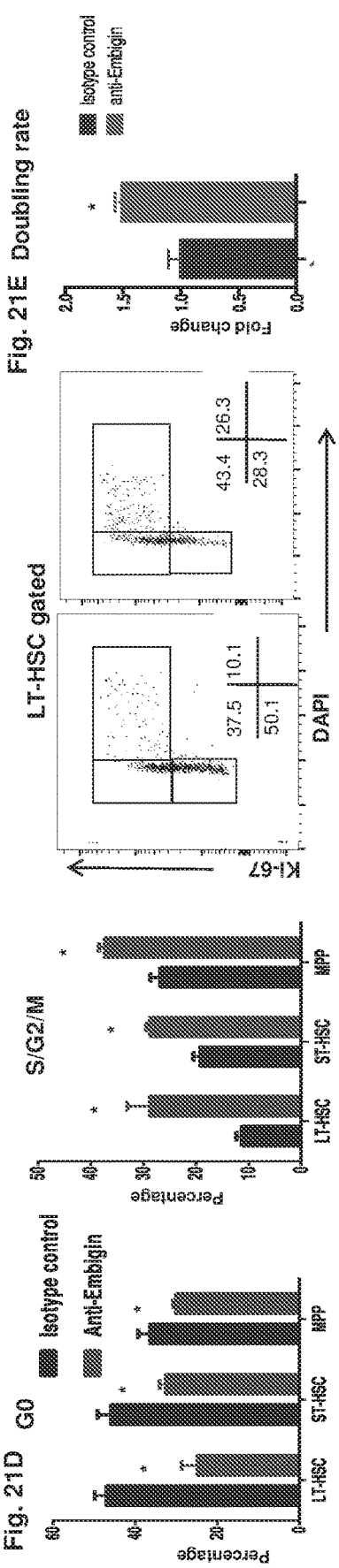

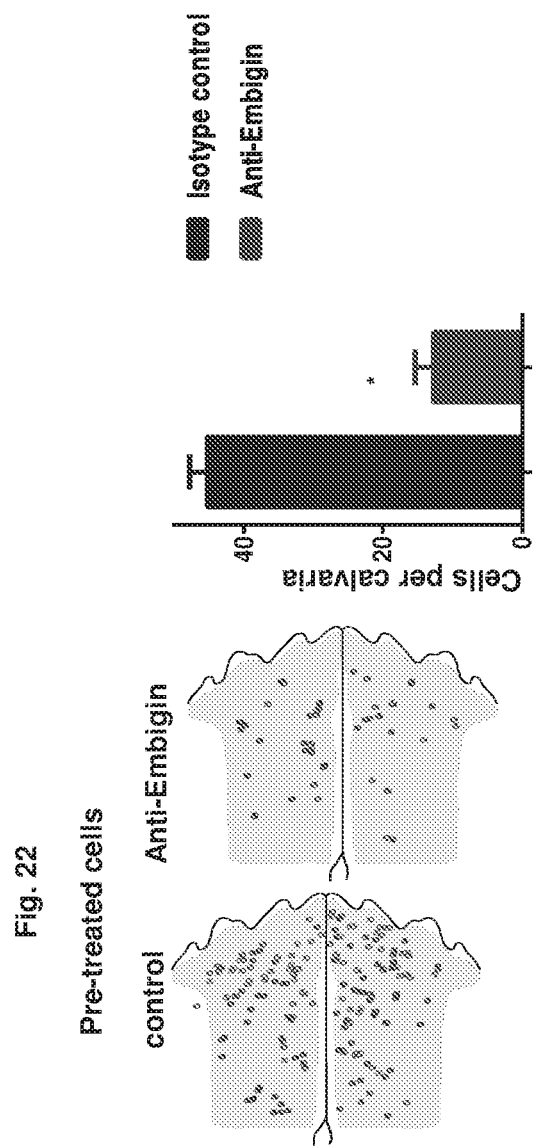

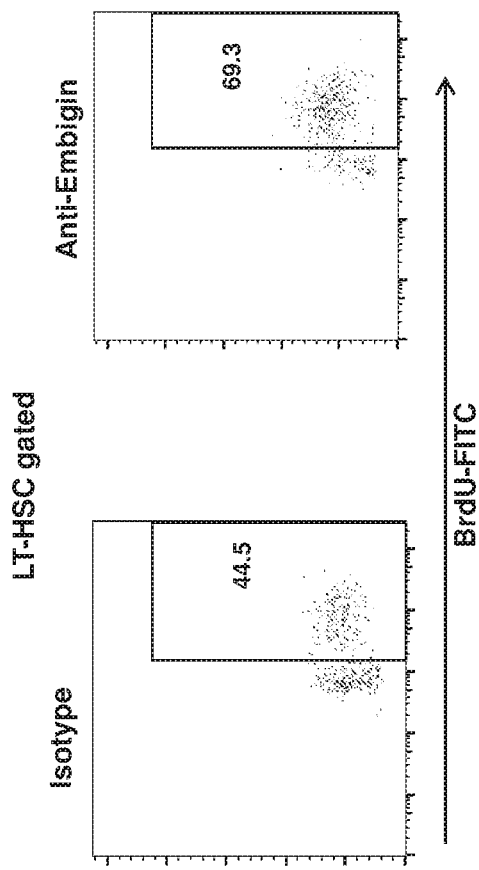
Fig. 23A
Fig. 23B
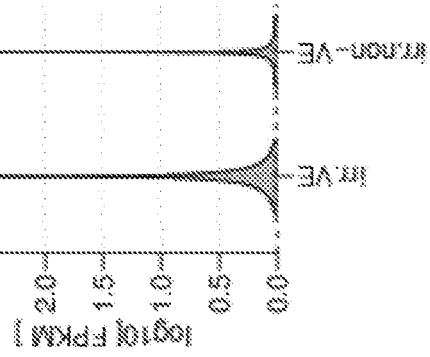
Fig. 24B
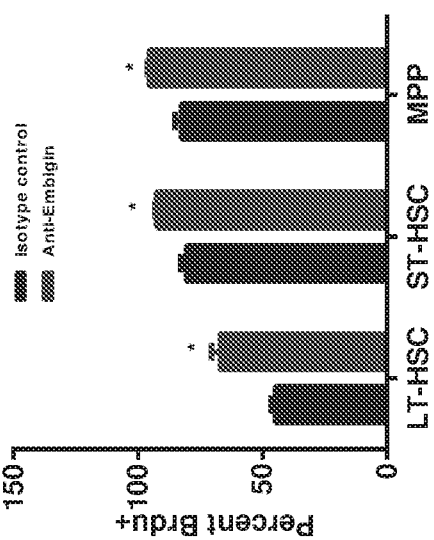
Fig. 24A
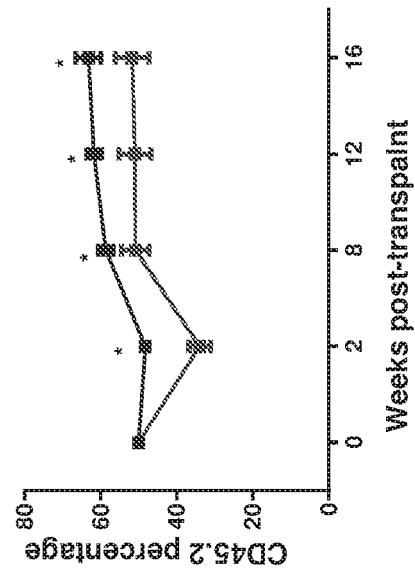

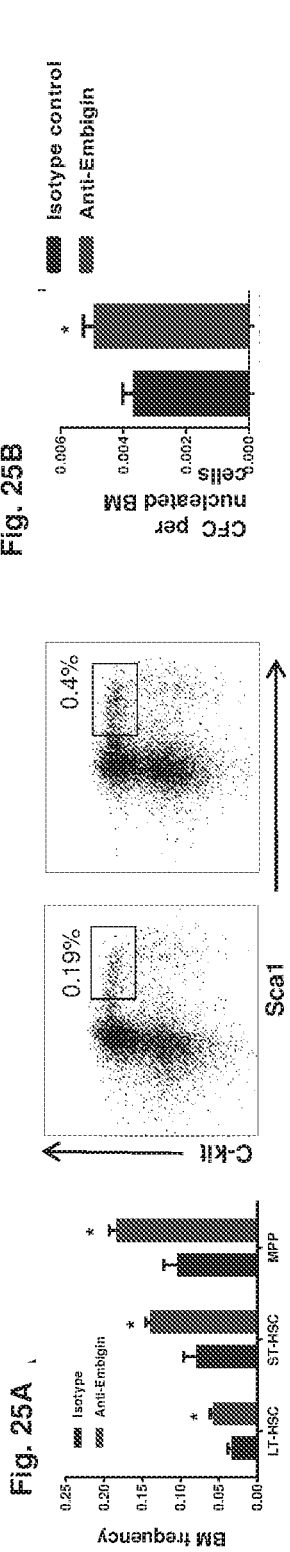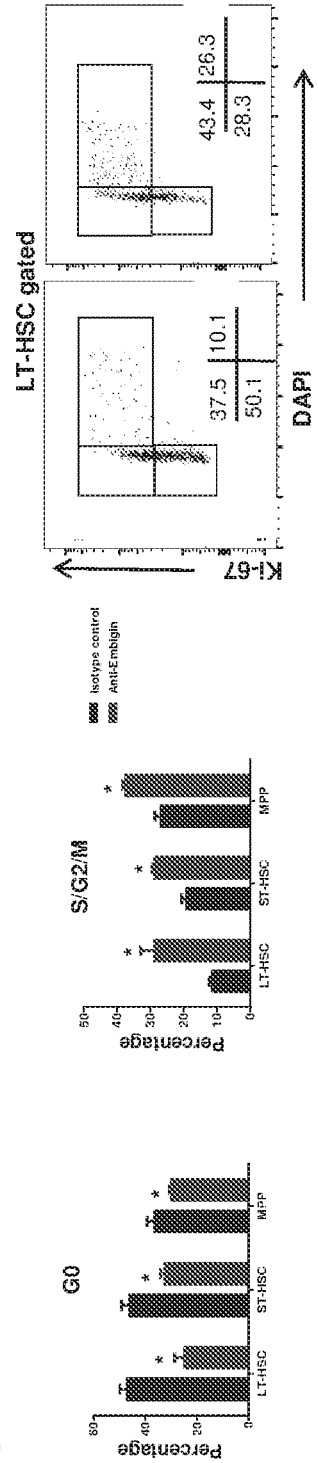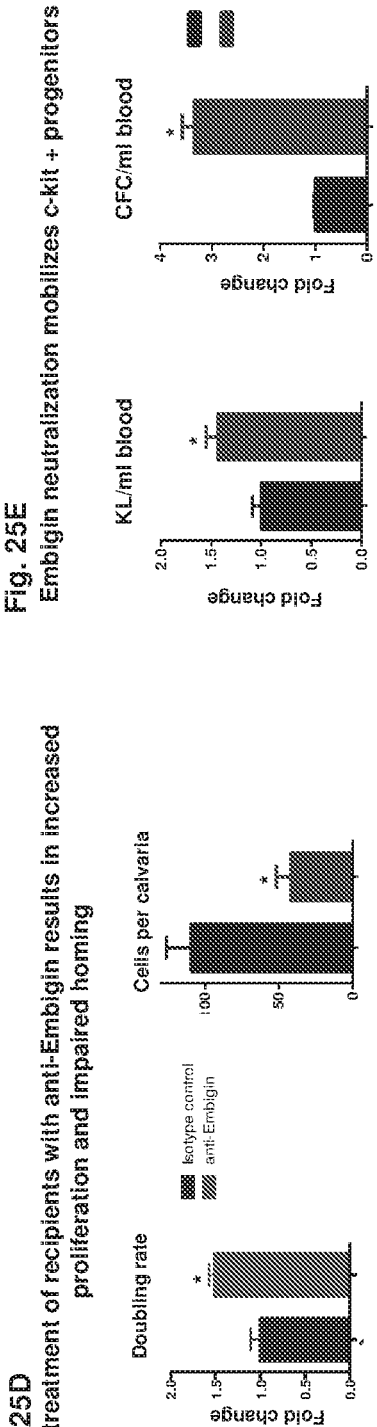

EMBIGIN INHIBITION FOR PROMOTION OF HEMATOPOIETIC STEM AND PROGENITOR CELL EXPANSION

CROSS REFERENCE TO RELATED APPLICATION

This application is a 35 U.S.C. § 371 National Phase Entry Application of International Application No. PCT/US2016/039969 filed Jun. 29, 2016, and which claims benefit under 35 U.S.C. § 119(e) of U.S. Provisional Application No. 62/186,075 filed Jun. 29, 2015, the contents of each of which are incorporated herein by reference in their entireties.

GOVERNMENTAL SUPPORT

This invention was made with government support under K25AG037596, R01DK050234-15A1, R01HL097794-03 and U01HL100402 awarded by the National Institutes of Health. The Government has certain rights in the invention.

FIELD OF THE DISCLOSURE

The present invention relates to the field of hematopoietic cell transplantation and reconstitution.

BACKGROUND OF THE DISCLOSURE

Hematopoiesis refers to the proliferation and differentiation process, in which different types of blood cells develop from multipotent stem cells having the capacity to proliferate and differentiate. Most of the blood cells in the blood are short lived and thus need to be replaced constantly throughout life. The levels of mature blood cells in the circulation can change rapidly in response to different environmental stress ranging from blood loss, infections, and the like. The major site of hematopoiesis in humans, after about 20 weeks of fetal life, is the bone marrow (BM), a tissue consisting of a heterogeneous population of cells including hematopoietic stem cells (HSCs), endothelial cells (ECs), and other stromal cells as well as cells involved in bone homeostasis, including chondroclasts and osteoblasts. Gerber and Ferrara, 2003, J. Mol. Med., 81:20-31.

Normal hematopoiesis is based on the dual functioning of multipotent stem cells. Extensive self-renewal maintains the population of undifferentiated stem cells, whereas differentiation results in the formation of various types of mature blood cells that are grouped into one of three major blood cell lineages: lymphoid, myeloid and erythroid cell lineages. The lymphoid lineage is comprised of B cells and T cells, which collectively function in antibody production and antigen detection, thereby functioning as a cellular and humoral immune system. The myeloid lineage is comprised of monocytes (macrophages), granulocytes (including neutrophils), and megakaryocytes, and monitors the bloodstream for antigens, scavenges antigens from the bloodstream, fights off infectious agents, and produces platelets that are involved in blood clotting. The erythroid lineage is comprised of red blood cells that carry oxygen throughout the body.

Hematopoietic system is hierarchically organized and consists of 3 main compartments—slow dividing long-term stem cells, very rapidly dividing progenitors and non-dividing mature cells (the "effector" compartment)—all of which have distinct cell-surface marker profile. Stem cells support hematopoiesis throughout the life-time, while progenitors have a capacity for massive short-term expansion in response to environmental stimuli such as infection or stress in order to generate a large number of mature blood cells. Long-term stem cells are absolutely required and sufficient for hematopoietic reconstitution following myeloablation. However, they are not as efficient at giving rise to mature cells as compared to more differentiating progenitors (Yang et al. Blood. 2005; 105:2717-2723). Cord blood, mobilized peripheral blood stem cells and bone marrow are currently used as a source of long-term hematopoietic stem cells in clinical bone marrow transplantation. All these products contain, together with stem cells, a variable proportion of hematopoietic progenitors.

There are a variety of disorders that involve the failure of a person's hematopoietic system, in which enhancement of proliferation of stem cells and progenitors (HSPC) would be therapeutic. In addition, post-transplant bone marrow aplasia is a major cause of morbidity and mortality after bone marrow transplant (BMT) Enhancing HSPC proliferation is an attractive strategy to improve the bone marrow function.

SUMMARY OF THE DISCLOSURE

One aspect of the invention relates to a method for enhancing hematopoietic reconstitution of a subject in need thereof comprising administering to the subject hematopoietic stem/progenitor cells (HSPCs), and administering to the subject a therapeutically effective amount of an inhibitor of Embigin to thereby contact the administered HSPCs and/or the microenvironment of the administered HSPCs.

In one embodiment of the methods described herein, administering the inhibitor is by a systemic route.

In one embodiment of the methods described herein, administering the inhibitor is by a route selected from the group consisting of enteral and parenteral.

In one embodiment of the methods described herein, administering the inhibitor is by intravenous administration.

In one embodiment of the methods described herein, administering the inhibitor is performed about 8 days after administering the HSPCs.

In one embodiment of the methods described herein, the inhibitor of Embigin is administered to the subject over a period of time from about 8 days to about 100 days directly after administration of the HSPCs.

In one embodiment of the methods described herein, administering the inhibitor is from about 8 days to about 50 days directly after administration of the HSPCs.

In one embodiment of the methods described herein, administering the inhibitor is from about 8 days to about 28 days directly after administration of the HSPCs.

In one embodiment of the methods described herein, administering the inhibitor is about 14 days directly after administration of the HSPCs.

In one embodiment of the methods described herein, the HSPCs are allogenic.

In one embodiment of the methods described herein, the HSPCs are autologous.

In one embodiment of the methods described herein, the HSPC are obtained from a donor subject treated with an inhibitor of Embigin and/or Interleukin 18 (IL-18) prior to harvest of the HSPCs to thereby expand the HSPCs.

Another aspect of the invention relates to a method for enhancing the hematopoiesis in a subject in need thereof comprising administering to the subject a therapeutically effective amount of an inhibitor of Embigin to thereby contact hematopoietic stem/progenitor cells (HSPCs) and/or the microenvironment of the HSPCs of the subject.

Another aspect of the invention relates to a method for hematopoietic stem/progenitor cells (HSPC) donation by a subject, comprising administering to the subject an effective amount of an inhibitor of Embigin to thereby induce expansion of HSPCs in the donor, and harvesting the HSPCs from the subject.

In one embodiment of the methods described herein, the administering step is from a period of about 1 day to about 5 days prior to harvest of the HSPCs.

In one embodiment of the methods described herein, the method further comprises administering to the subject an effective amount of an inhibitor of Interleukin 18 (IL18) to thereby induce expansion of early hematopoietic progenitor cells.

Another aspect of the invention relates to a method for enhanced hematopoietic reconstitution in a subject in need thereof comprising administering to the subject hematopoietic stem/progenitor cells (HSPC) obtained from a donor subject, wherein the donor subject was treated with an inhibitor of Embigin to thereby expand HSPCs prior to harvest of the HSPCs from the donor.

In one embodiment of the methods described herein, the donor subject was further treated with an inhibitor of Interleukin 18 (IL-18) to thereby expand early hematopoietic progenitor cells prior to harvest of the HSPCs from the donor.

In one embodiment of the methods described herein, the donor subject is treated with the inhibitor of Embigin for a period of from about 1 day to about 10 days directly prior to harvest of the HSPCs. In one embodiment of the methods described herein, the period is from about 1 day to about 5 days directly prior to harvest of the HSPCs. In one embodiment of the methods described herein, the period is about 5 days directly prior to harvest of the HSPCs.

In one embodiment of the methods described herein, the treatment of the donor subject is by administration of the inhibitor of Embigin and/or the inhibitor of IL-18 to the donor subject by a method selected from the group consisting of enteral and parenteral.

In one embodiment of the methods described herein, the HSPCs are obtained from bone marrow, blood, placenta, or umbilical cord of the donor.

In one embodiment of the methods described herein, the inhibitor of Embigin is selected from the group consisting of a neutralizing antibody against Embigin, a soluble form of Embigin, and a fragment of Embigin.

In one embodiment of the methods described herein, the inhibitor of Embigin is a neutralizing antibody against Embigin.

In one embodiment of the methods described herein, the neutralizing antibody against Embigin is a monoclonal antibody.

In one embodiment of the methods described herein, the antibody is a humanized antibody.

In one embodiment of the methods described herein, the antibody is a human antibody.

In one embodiment of the methods described herein, the method further comprises administration of a therapeutically effective amount of an inhibitor of IL-18, to thereby inhibit IL-18 interaction with IL-18R molecules present on the administered HSPC.

In one embodiment of the methods described herein, the inhibitor of IL-18 is selected from the group consisting of IL-18 binding protein, an antibody against IL-18, an antibody against an IL-18 receptor subunits, an inhibitor of the IL-18 signaling pathway, an antagonist of IL-18 which competes with IL-18 and blocks the IL-18 receptor, an inhibitor of caspase-1 (ICE), an IL-18 isoform, an IL-18 mutein, an IL-18 fused protein, an IL-18 functional derivative, an IL-18 active fraction, and an IL-18 circularly permutated derivative thereof inhibiting the biological activity of IL-18.

Definitions

As used herein, the term "hematopoiesis" refers to the formation and development of blood cells. In the embryo and fetus it takes place in a variety of sites including the liver, spleen, thymus, lymph nodes, and bone marrow; from birth throughout the rest of life it is mainly in the bone marrow with a small amount occurring in lymph nodes.

As used herein, the term "hematopoietic reconstitution" refers to the reconstruction of the hematopoietic system, the bodily system of organs and tissues, primarily the bone marrow, spleen, tonsils, and lymph nodes, involved in the production of blood. Reconstitution also meant to restore, rebuild, recreate, regenerate, or reassemble the hematopoietic system.

HSPC contain a mixture of long-term hematopoietic stem cells and early progenitor hematopoietic cells.

An "effective amount" as the term is used herein, is used to refer to an amount that is sufficient to produce at least a reproducibly detectable amount of the desired results. In the context of the invention, effective amounts are amounts that inhibit Embigin activity as described herein. One example of an effective amount is an amount that results in substantial inhibition of the activity in the HSPCs and in the microenvironment. Substantial inhibition may comprise inhibition of greater than 10%, 20%, 30%, 40%, 50%, 60%, 70%, 80%, or 90% of detectable activity such as that in an identically treated control that is not exposed to the inhibitor. Such inhibition can be measured directly or indirectly. Direct measurement involves identification of binding, or receptor binding, or other direct measurements of Embigin activity such as cell signaling or cell adhesion function. Indirect measurement involves quantitation of overall cellular activity, such as cellular proliferation and differentiation or other measurements of Embigin activity such as the assays provided herein. An effective amount will vary with the specific conditions and circumstances. Such an amount can be determined by the skilled practitioner for a given situation. The effective amounts can be provided all at once in a single administration or in fractional amounts that provide the effective amount in several administrations.

The term "therapeutically effective amount" refers to an amount that is sufficient to effect a therapeutically significant reduction in one or more symptoms of the condition when administered to a typical subject who has the condition. A therapeutically significant reduction in a symptom or complication resulting from the transplant, or increase in re-populating neutrophils and lymphocytes in an HSPC transplant recipient is, e.g. about 10%, about 20%, about 30%, about 40%, about 50%, about 60%, about 70%, about 80%, about 90%, about 100%, or more (e.g, 1.5 fold, 2 fold, 3 fold, 4 fold, 5 fold, 10 fold, 25 fold, 50 fold, 100 fold, etc.) as compared to a control or non-treated subject. The term "therapeutically effective amount" refers to the amount of an agent determined to produce any therapeutic response in a subject. For example, a therapeutically effective amount of an inhibitor of Embigin may increase the number of neutrophils and lymphocytes in an HSPC transplant recipient over time as compared to a similar transplant recipient who has not received the inhibitor. This is expected to occur during the early stages of repopulation, the critical time period being up to 100 days post-transplant (e.g., within days 1, 2, 3, 4, 5, 5-10, or within 1, 2, 3, or 4 weeks, 1, 2, or 3 months). This will reduce or eliminate the development of complications following transplant and reduce mortality from complications. Complications following transplant include, without limitation, graft-vs-host disease (GvHD), bacterial infections, fungal infections, viral infections, gastrointestinal and hepatic complications, neurologic complications, and pulmonary complications.

Treatments that are therapeutically effective within the meaning of the term as used herein, include treatments that reduce or eliminate complications experienced by the transplant recipients within the critical post-transplant time frame discussed herein. Such therapeutically effective amounts are readily ascertained by one of ordinary skill in the art. Thus, to "treat" means to deliver such an amount.

The precise determination of what would be considered a therapeutically effective amount may be based on factors individual to each subject, including their size, age, injury, and/or disease or injury being treated, and amount of time since the injury occurred or the disease began. One skilled in the art will be able to determine the therapeutically effective amount for a given subject based on these considerations which are routine in the art.

The term "treat" or "treatment" refers to therapeutic treatment wherein the object is to eliminate or lessen symptoms. Beneficial or desired clinical results include, but are not limited to, elimination of symptoms, alleviation of symptoms, diminishment of extent of condition, stabilized (i.e., not worsening) state of condition, delay or slowing of progression of the condition.

Preferably, the subject is a mammal. The mammal can be a human, non-human primate, mouse, rat, dog, cat, horse, or cow, but are not limited to these examples. Mammals other than humans can be advantageously used as subjects that represent animal models of disorders associated with unwanted activity. In addition, the methods and compositions described herein can be used to treat domesticated animals and/or pets.

The terms "patient", "subject" and "individual" are used interchangeably herein, and refer to an animal, particularly a human, to whom treatment is provided. This includes human and non-human animals. The term "non-human animals" and "non-human mammals" are used interchangeably herein includes all vertebrates, e.g., mammals, such as non-human primates, (particularly higher primates), sheep, dog, rodent (e.g. mouse or rat), guinea pig, goat, pig, cat, rabbits, cows. In one embodiment, the subject is human. In another embodiment, the subject is an experimental animal or animal substitute as a disease model. "Mammal" refers to any animal classified as a mammal, including humans, non-human primates, domestic and farm animals, and zoo, sports, or pet animals, such as dogs, cats, cattle, horses, sheep, pigs, goats, rabbits, etc. Patient or subject includes any subset of the foregoing, e.g., all of the above, but excluding one or more groups or species such as humans, primates or rodents. A subject can be male or female. A subject can be a fully developed subject (e.g., an adult) or a subject undergoing the developmental process (e.g., a child, infant or fetus). In one embodiment, the subject has been previously diagnosed with a disorder that necessitates the therapeutic intervention. In one embodiment, the subject has been determined to have a predisposition to develop the disorder that necessitates the therapeutic intervention.

The term "antibody" herein is used in the broadest sense and specifically covers human, non-human (e.g. murine) and humanized monoclonal antibodies (including full length monoclonal antibodies), polyclonal antibodies, multispecific antibodies (e.g., bispecific antibodies), single chain antibodies and antibody fragments so long as they exhibit the desired biological activity.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intra-chain disulfide bridges. Each heavy chain has at one end a variable domain (VH) followed by a number of constant domains. Each light chain has a variable domain at one end (VL) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework region (FR). The variable domains of native heavy and light chains each comprise four FRs (FR1, FR2, FR3 and FR4, respectively), largely adopting a .beta.-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669). The constant domains are not involved directly in binding an antibody to an antigen, but exhibit various effector functions, such as participation of the antibody in antibody-dependent cellular toxicity.

The term "hypervariable region" when used herein refers to the amino acid residues of an antibody which are responsible for antigen binding. The hypervariable region comprises amino acid residues from a "complementarity determining region" or "CDR" (i.e. residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26-32 (L1), 50-52 (L2) and 91-96 (L3) in the light chain variable domain and 26-32 (H1), 53-55 (H2) and 96-101 (H3) in the heavy chain variable domain; Chothia and Lesk, 1987, J. Mol. Biol. 196:901-917). "Framework" or "FR"

residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen.

"Fv" is the minimum antibody fragment that contains a complete antigen-recognition and binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxyl terminus of the heavy chain CH1 domain including one or more cysteine(s) from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (i), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1, and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

"Antibody fragments" comprise a portion of a full-length antibody, generally the antigen binding or variable domain thereof. Examples of antibody fragments include Fab, Fab', F(ab')$_2$, and Fv fragments; diabodies; linear antibodies; single-chain antibody molecules; and multi-specific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations that typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., 1975, Nature 256:495, or may be made by recombinant DNA methods (see, e.g., U.S. Pat. No. 4,816,567). The "monoclonal antibodies" may also be isolated from phage antibody libraries using the techniques described in Clackson et al., 1991, Nature 352:624-628 and Marks et al., 1991, J. Mol. Biol. 222:581-597, for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., 1984, Proc. Natl. Acad. Sci. USA, 81:6851-6855).

"Humanized" forms of non-human (e.g., murine) antibodies are chimeric antibodies that contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or non-human primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable regions correspond to those of a non-human immunoglobulin and all or substantially all the FRs are those of a human immunoglobulin sequence. The FRs may optionally be those of a consensus or modified consensus sequence, as described, for example, in Carter et al., U.S. Pat. No. 6,054,297. The humanized antibody optionally also will comprise at least a portion of an immunoglobulin constant region (Fc), typically that of a human immunoglobulin. For further details, see Jones et al., 1986, Nature, 321:522-525; Reichmann et al., 1988, Nature, 332:323-329; and Presta, 1992, Curr. Op. Struct. Biol., 2:593-596.

"Single-chain Fv" or "sFv" antibody fragments comprise the VH and VL domains of antibody, wherein these domains are present in a single polypeptide chain. Generally, the Fv polypeptide further comprises a polypeptide linker between the VH and VL domains which enables the sFv to form the desired structure for antigen binding. For a review of sFv see Pluckthun in The Pharmacology of Monoclonal Antibodies, vol. 113, Rosenburg and Moore eds. Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., 1993, Proc. Natl. Acad. Sci. USA, 90:6444-6448.

The expression "linear antibodies" refers to the antibodies described in Zapata et al., 1995, Protein Eng., 8(10):1057-1062. Briefly, these antibodies comprise a pair of tandem Fd segments (VH-CH1-VH-CH1) which form a pair of antigen binding regions. Linear antibodies can be bispecific or monospecific.

The term "epitope" is used to refer to binding sites for (monoclonal or polyclonal) antibodies on antigens.

BRIEF DESCRIPTION OF THE DRAWINGS

FIG. 1A shows the DiI-labeled adult bone marrow LKS CD34-Flk2-LT-HSCs were intravenously injected into irradiated col2.3GFP pups (P2). Forty-eight hours later, fresh sections of the femori were obtained, individual proximal and distal OLCs were identified and harvested for single cell RNA-Seq analysis. Selected differentially expressed genes were validated in-vivo.

FIG. 1B shows the classification of individual OLCs based on the top 200 differentially expressed genes. Each row represents a gene, with the most likely gene expression levels indicated by darker shades of gray to black for high and lighter shades to white for low to absent.

FIG. 1C shows an unbiased genome-wide classification of proximal and distal OLCs. The receiver-operator curve is shown for the Support Vector Machine classification where all successive pairs of cells (one proximal and one distal) were classified based on the training data provided by other cells (P<0.005).

FIGS. 1D and 1E show the expression analysis of known niche-derived HSPC regulators and OLC maturation genes. The violin plots show the posterior distribution of the expression fold-difference (y-axis, $\log_2$ scale) for each gene, with the shaded area marking the 95% confidence region. The horizontal solid red lines show the most likely fold-change value.

FIG. 2A shows the proximal GFP+ OLC in white areas was identified based on proximity to the DiI-labeled HSPC.

FIG. 2B shows that following in-situ enzymatic dissociation, the HSPC was dislodged from its original location, other hematopoietic cells became loose and OLCs partially detached from the endosteal surface.

FIG. 2C shows that proximal OLC was aspirated into a micropipette.

FIG. 4 shows experimental results of gene set enrichment analysis (GSEA) of differentially expressed genes between proximal and distal OLCs. GSEA plots referring to expression of gene sets "Surface proteins" and "Immune response" in proximal OLCs (p<0.0005) are shown.

FIG. 5A-5E collectively show the experimental results that indicate isolation and characterization of col2.3GFP+ Embiginhigh VCAM1+ OLC subset (VE cells).

FIG. 5A shows Embigin expression in proximal and distal OLCs.

FIG. 5B shows the gating strategy for FACS-based isolation of VE (CD45-Ter119-GFP+ VCAM1+Embigin+) and non-VE OLCs (remaining CD45-Ter119-GFP+) from long bones of adult col2.3GFP mice. The animals were irradiated and injected with LKS CD34-Flk2-LT-HSCs, lin-kit+Sca– progenitors or PBS.

FIG. 5C shows the RNA-Seq profiling and classification of FACS-sorted VE and non-VE cells from the three experimental groups described above using 200-gene proximal OLC signature (FIG. 2B).

FIG. 5D shows the Gene Set Enrichment Analysis (GSEA) of genes encoding for cell-cell adhesion functions (GO:0016337) in VE cells from LT-HSC injected vs saline-injected group FIG. 5E shows the effect VE and non-VE fraction on HSPC growth in vitro, as assessed by growth kinetics and CFC number per well at 72 hrs (n=3).

FIG. 8A-8D collectively show the experimental results of flow cytometric and transcriptional comparison of VE cells and N-cadherin-positive osteoblastic cells. N-cadherin-positive and N-cadherin-negative gates were established as shown in (FIG. 8A) and applied to the VE fraction (FIG. 8B). Expression of niche factors (FIG. 8C) and Wnt-ligands (FIG. 8D) in VE cells versus N-cadherin+ cells was assessed by RNA-Seq.

FIG. 9A-9G collectively show the experimental results of in vivo analysis of Interleukin 18 (IL18) function in HSPC regulation.

FIG. 9A shows that IL18 is expressed in proximal and distal OLCs.

FIG. 9B shows that BrdU was incorporation by HSPC in IL18KO mice (n=5).

FIG. 9C shows IL18 receptor expression in HSPC. Representative histograms are shown (n=3). A comparable cell population from IL18R KO mouse was used as a negative control (shaded histogram).

FIG. 9D shows the flow cytometric assessment of multi-lineage response to 5-FU in IL18KO mice. The statistical significance was assessed by ANOVA. Boxplots illustrating log ratios of cell numbers between 5FU-treated and vehicle-treated animals in WT and IL18 groups are shown (n=7).

FIG. 9E shows enumeration of apoptotic LKS cells and lin-negative cells in WT animals pre-treated with rIL18 prior to 5-FU exposure (n=5).

FIG. 9F shows enhanced early myeloid and lymphoid reconstitution in IL18KO mice following transplantation of LKS cells (n=7 per group).

FIG. 9G shows the effect of VE cells and non-VE cells on HSPC proliferation in vitro, as assessed by HSPC growth kinetics and CFC number (n=3).

FIG. 10A-10C collectively show the baseline analysis of peripheral blood and the bone marrow in IL18KO mice.

FIG. 10A shows a table summarizing the peripheral blood analysis (n=12 per group).

FIG. 10B shows the gating strategy and quantification of LT-HSC, ST-HSC and MPP (n=12 per group).

FIG. 10C shows the quantification of mature cell frequency (n=6 per group).

FIG. 11 shows BrdU incorporation in IL18KO mice (n=5). Data from representative experiment are shown (n=5).

FIG. 12A-12B show the experimental design (FIG. 12A) and flow cytometric assessment of the bone marrow (FIG. 12B) in WT animals pretreated with recombinant IL18 and exposed to 5FU (n=5).

FIG. 13A shows the quantification and representative FACS plots from cell cycle studies in newborn IL18KO mice.

FIG. 13B shows the flow cytometric assessment of primitive hematopoietic subsets in P1 pups following in-utero exposure to Busulphan (n=6).

FIG. 14A-14C collectively show the assessment of short-term multi-lineage post-transplant reconstitution in IL18KO recipients of WT bone marrow.

FIG. 14A shows the experimental design.

FIG. 14B shows the peripheral blood analysis of donor-derived cells during 16 weeks post-transplant.

FIG. 14C shows the WBC and lineage analysis 4 weeks post-transplant (*p<0.05, n=5 per group).

FIG. 15A shows the experimental design.

FIG. 15B shows the peripheral blood analysis of donor-derived cells during the first 4 weeks post-transplant (*p<0.05, n=7 per group).

FIG. 16A-16C collectively show intravital microscopy of transplanted WT LKS in IL18KO recipients. Quantification of total number of cells (FIG. 16A), cell doublets 24 hours after transplantation (FIG. 16B) and the shortest three-dimensional distance (in microns) between tdTomato+ cells and the endosteal surface (FIG. 16C) (*p<0.05, n=6).

FIG. 20A-20B collectively show the experimental results that indicate VE cells are present exclusively in the col2.3GFP+ fraction. GFP-negative and GFP-positive gates were established as shown (FIG. 20A) and applied to the VE-fraction. All VE cells fall within GFP+ gate (FIG. 20B).

FIG. 21A-21E collectively show the experimental results of in vivo analysis of Embigin function in HSPC regulation.

FIG. 21A shows the enumeration of myeloid (kit+ lin− Sca1−) progenitor cell frequency and CFC number in peripheral blood following treatment with anti-Embigin or isotype control antibody (p<0.05, n=5).

FIG. 21B shows the quantification of HSPC homing in animals pre-treated with anti-Embigin antibody or isotype control by intra-vital microscopy (p<0.05, n=4). Each dot represents location of an individual cell from four individual mice (n=4, p<0.05).

FIG. 21C shows the HSPC and CFC frequency following injection of anti-Embigin.

FIG. 21D shows the cell cycle studies in anti-Embigin or isotype control-injected mice.

FIG. 21E shows the proliferation of transplanted LKS cells in animals pre-treated with anti-Embigin.

FIG. 22 shows the quantification of LKS cell homing following pre-incubation of donor LKS cells with neutralizing antibody against Embigin by intravital microscopy. Each dot represents location of an individual cell from four individual mice (n=4, p<0.05).

FIG. 23A-23B collectively show the experimental results representative of BrdU incorporation in HSPC from WT mice injected with anti-Embigin or isotype control antibody. Cumulative quantification (FIG. 23A) and representative flow plots (FIG. 23B) are shown (n=5).

FIGS. 24A and 24B collectively show the experimental results that indicate peripheral blood chimerism following competitive transplantation of whole BM cells derived from anti-Embigin or isotype control-injected mice (n=8-9 per group, p<0.05).

FIG. 24A shows the competitive (1:1) transplant of bone marrow cells treated with anti-Embigin or isotype control.

FIG. 24B shows the Changes in niche factor expression in VE cells following irradiation. Data normalized read counts (FKPM) are shown.

FIG. 25A-25E collectively show the experimental results from the in vivo analysis of Embigin function in HSPC regulation. HSPC (FIG. 25A) and CFC frequency (FIG. 25B) following injection of neutralizing antibody against Embigin. Results indicate Embigin neutralization leads to increased HSPC frequency.

FIG. 25C shows the cell cycle studies in anti-Embigin or isotype control-injected mice. Results indicate Embigin neutralization leads to more active cycling of primitive hematopoietic cells.

FIG. 25D shows the quantification of HSPC proliferation and homing in animals pre-treated with anti-Embigin antibody or isotype control by intra-vital microscopy (p<0.05, n=4). Results indicate pre-treatment of recipients with anti-Embigin results in increased proliferation and impaired homing.

FIG. 25E shows the enumeration of kit+lin− Sca1− cell frequency and CFC number in peripheral blood following treatment with anti-Embigin or isotype control antibody (p<0.05, n=5). Results indicate Embigin neutralization mobilizes c-kit and progenitors.

DETAILED DESCRIPTION OF THE DISCLOSURE

Figure 1:
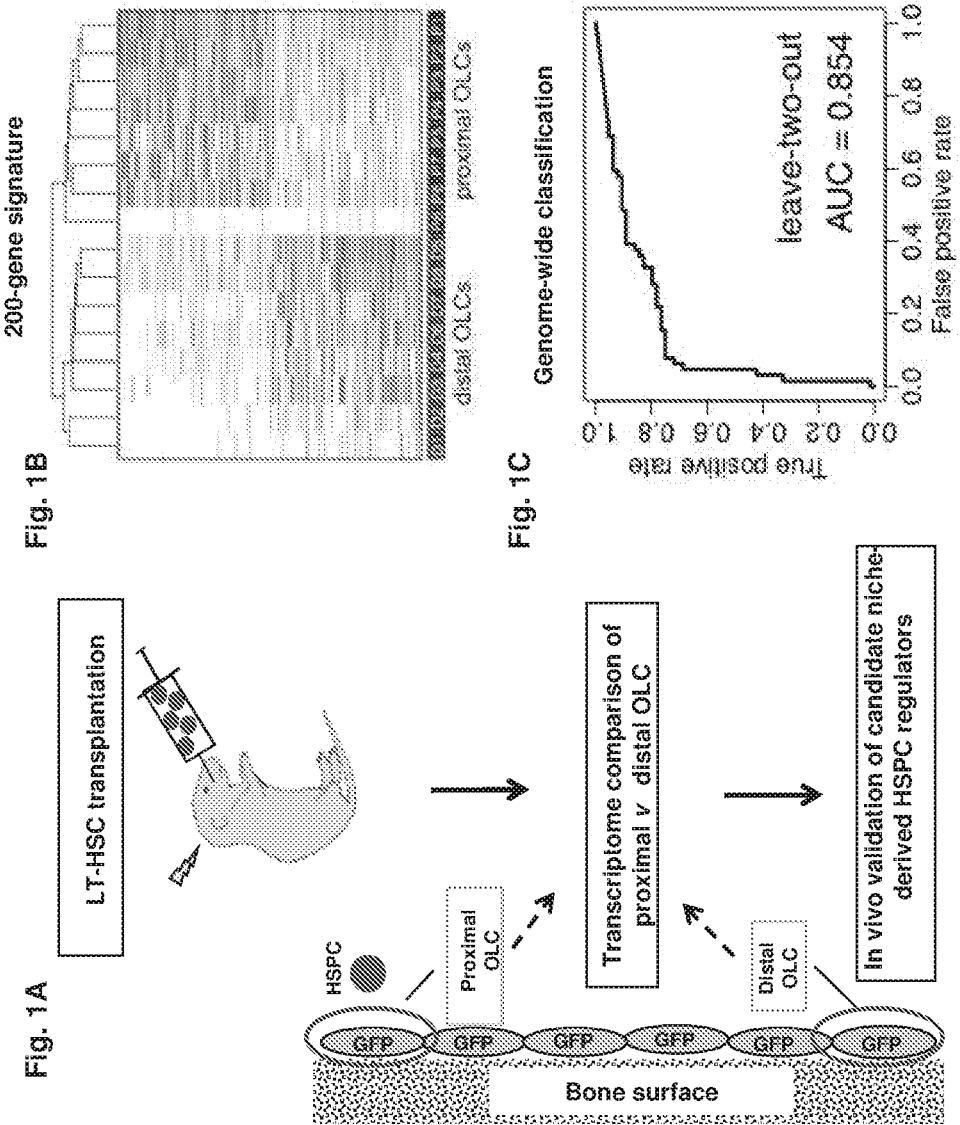
FIG. 1A-1E collectively show the experimental results that indicate proximity-based single cell analysis of the bone marrow niche.

Aspects of the invention relate to the discovery that the cell adhesion molecule Embigin has a regulatory function in HSPC quiescence. Inhibition of Embigin results in mobilization of myeloid progenitors and colony-forming cells into the blood, and a higher frequency and proliferative activity of HSPC. Pretreating irradiated recipients of donated HSPC with Embigin antibody resulted in increased proliferation of the transplanted bone marrow cells. Inhibiting Embigin has a proliferative effect on short-term progenitors and also LT-HSCs, and affects cellular quiescence. Without being bound by theory, it is thought that the inhibitory effect of Embigin is not limited to a distinct hematopoietic cell subset, but rather that it regulates a specific cell state. As such, inhibiting Embigin of HSPCs and in the microenvironment of the HSPCs (e.g., the bone marrow) induces proliferation and expansion of a variety of cells types found in bone marrow. Embigin inhibition leads to HSPC expansion by both inducing the expansion of early hematopoietic progenitors and also inducing expansion of the hematopoietic stem cells. These results indicate that therapeutic inhibition of Embigin can be used to reconstitute a failing hematopoietic system and can be applied to existing methods for hematopoietic reconstitution (such as bone marrow transplant) to enhance the proliferation of HSPC and/or development into neutrophils and lymphocytes and induce expansion of HSPC in a subject to accelerate post-transplant recovery. Such accelerated recovery will reduce the risk of infection and hemorrhagic complications, and in turn reduce post-transplant morbidity and mortality.

One aspect of the invention relates to a method for hematopoietic reconstitution in a subject. The method involves administering to the subject hematopoietic stem/progenitor cells (HSPC) and administering to the subject a therapeutically effective amount of an inhibitor of Embigin. The inhibitor is administered by a route and in a sufficient amount to thereby contact the HSPCs and/or the microenvironment of HSPCs in the subject and to thereby promote enhanced proliferation and expansion of the HSPCs in vivo. The expansion promoted is both to early hematopoietic progenitors and also hematopoietic stem cells. The hematopoietic reconstitution in the subject which would otherwise occur in the absence of the inhibitor is thereby enhanced by the activity of the inhibitor in that the reconstitution (short term and/or long term) occurs faster and/or more completely (e.g, with enhanced differentiation into a broader range of cell types) than otherwise would have occurred in the absence of the inhibitor.

The microenvironment of the HSPC includes the osteolineage cells proximal to HSPCs (e.g., transplanted or endogenous) and other cells such as perivascular cells, endothelial cells, adipocytes, megakaryocytes, macrophages, Schwann cells and mesenchymal stem cells.

It is thought that in some situations inhibition of Embigin will have beneficial effects on a subject's failing hematopoietic system in the absence of transplanted HSPC. In this way, the inhibitor will act on the subjects' existing cells to induce HSPC expansion (e.g., to therapeutically treat bone marrow failure). As such, another aspect of the invention relates to a method for enhancing the hematopoiesis in a subject in need thereof comprising administering to the subject a therapeutically effective amount of an inhibitor of Embigin to thereby contact hematopoietic stem/progenitor cells (HSPCs) and/or the microenvironment of the HSPCs of the subject. In one embodiment, the subject is also treated with an inhibitor of IL-18 to thereby induce expansion of early hematopoietic progenitor cells.

A recipient subject in the methods described herein can be anyone in need of hematopoietic reconstitution or anyone with reduced number of white blood cells in peripheral blood. Such subjects include, without limitation, subjects with hematopoietic cancer such as leukemia and lymphoma, subjects with myelosuppression or myeloablation, such as those who have undergone cytoreductive therapy (e.g., chemotherapy or radiation therapy). The recipient subject may suffer from diseases and disorders including, without limitation, leukopenia of various origins including, congenital leukopenia, childhood or adult cyclic neutropenia, post-infective neutropenia, and myelodysplastic syndrome and aplastic anemia (congenital and acquired). Subjects suitable as recipients include those in which their entire hematopoietic system is ablated, and also those with reduced intensity conditioning. Reduced intensity conditioning does not result in complete myeloablation and is used in patients that are older, in patients who are in complete remission, and in patients with acquired aplastic anemia.

Timing of Inhibitor Administration

In one embodiment, the Embigin inhibitor can be coordinated with administration of donor hematopoietic stem/progenitor cells (HSPC) to facilitate reconstitution of the subject, as discussed herein. Administration of the inhibitor to the recipient subject may be prior to, concurrent with, or after administration of the HSPC.

It may be advantageous for administration to be ongoing over a period of time. If the subject is also to receive HSPCs, the inhibitor can be administered beginning prior to, concurrent with or after administration of the HSPCs. Such ongoing administration could be by way of multiple administration time points. In one embodiment, the inhibitor is administered to the subject for a period of from about 1 day to about 5 days (e.g., about 5, 4, 3, 2 or 1 days). In one embodiment, the inhibitor is administered to the subject for a period of from about 5 days to about 10 days (e.g., about 10, 9, 8, 7, or 6 days). In one embodiment, the inhibitor is administered to the subject for a period of from about 10 days to about 20 days (e.g., about 20, 19, 18, 17, 16, 15, 14, 13, 12, or 11 days). In one embodiment, the inhibitor is administered to the subject for a period of from about 20 days to about 30 days (e.g., about 30, 29, 28, 27, 26, 25, 24, 23, 22, or 21 days). Benefit may also be obtained from administration on a regular basis up to about day 50 or 100 (e.g., of donated HSPC administration). Administration of the inhibitor at the time of administration of the HSPC encompasses administration concurrently with the HSPCs, directly prior to (e.g., within an hour prior), directly following administration of the HSPC (e.g., within about 1-24 hours), and after a period of time that allows for homing of the HSPCs to take place. In one embodiment, administration is after a period of about 6 to 14 days following administration of the HSPCs. In one embodiment, administration of the Embigin inhibitor is begun at about 6 days, 7 days, 8 days, 9 days, 10 days, 11 days, 12 days, 13 days, 14 days, or more after administering the HSPCs. In one embodiment, the inhibitor is administered to the subject for a period of from about 8 days to about 100 days after administering the HSPCs. In other embodiments, the inhibitor is administered to the subject for a period of from about 6 days to about 100 days, about 6 days to about 90 days, about 6 days to about 80 days, about 6 days to about 70 days, about 6 days to about 60 days, about 6 days to about 50 days, about 6 days to about 40 days, about 6 days to about 30 days, about 6 days to about 28 days, about 6 days to about 20 days, about 6 days to about 10 days, about 8 days to about 90 days, about 8 days to about 80 days, about 8 days to about 70 days, about 8 days to about 60 days, about 8 days to about 50 days, about 8 days to about 40 days, about 8 days to about 30 days, about 8 days to about 28 days, about 8 days to about 20 days, about 10 days to about 100 days, about 10 days to about 90 days, about 10 days to about 80 days, about 10 days to about 70 days, about 10 days to about 60 days, about 10 days to about 50 days, about 10 days to about 40 days, about 10 days to about 28 days, about 10 days to about 30 days, about 10 days to about 20 days, about 12 days to about 100 days, about 12 days to about 90 days, about 12 days to about 80 days, about 12 days to about 70 days, about 12 days to about 60 days, about 12 days to about 50 days, about 12 days to about 40 days, about 12 days to about 28 days, about 12 days to about 30 days, about 12 days to about 20 days, about 14 days to about 100 days, about 14 days to about 90 days, about 14 days to about 80 days, about 14 days to about 70 days, about 14 days to about 60 days, about 14 days to about 50 days, about 14 days to about 40 days, about 14 days to about 28 days, about 14 days to about 30 days, about 14 days to about 20 days after administering the HSPCs. Administration of the inhibitor can be repeated after the first dose as necessary to produce the desired effect.

Administration concurrently with the HSPCs may also include combining the HSPCs with the inhibitor and administering the combination to the subject.

Administration of the inhibitor to the subject prior to administration of the HSPC is expected to have some beneficial effect. Administration for a period of from about 1 day up to about 5 days (e.g., about 5, 4, 3, 2 or 1 day) prior to administration of the HSPCs is envisioned. In other embodiments, the administration period is repeated daily for up to 5 days. In one embodiment, administration of the inhibitor prior to receipt is combined with administration at the time of receipt and/or ongoing administration for a period of time as described herein.

Administration of a combination of two or more Embigin inhibitors such as those described herein is also envisioned. The Embigin inhibitor can also be coordinated with administration of one or more additional agents (e.g., IL-18 inhibitor) to facilitate reconstitution of the subject, as discussed herein. The inhibitor combination can be administered with donor HSPCs or in the absence of donor HSPCs.

Routes of Administration

The route of administration of the compositions described herein (e.g., the Embigin inhibitor) is by methods sufficient to contact the active agents with the HSPC and/or with the microenvironment of the HSPC (administered and/or endogenous). These routes apply equally to administration to a donor of HSPCs prior to harvest, discussed below. The compositions of the present invention may be administered in a number of ways depending upon whether local or systemic treatment is desired. For systemic treatment, both enteral (e.g., oral) and parenteral (e.g., intravenous) administration are envisioned. The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like. The compounds of the invention can be administered by injection or by gradual infusion over time and can be delivered by peristaltic means. Parenteral administration includes intravenous drip, subcutaneous, intraperitoneal or intramuscular injection, pulmonary administration, e.g., by inhalation or insufflation.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

In one embodiment, administration results in contacting of the target HSPCs (e.g., HSPCs within the donor prior to donation, or HSPCs in the transplant recipient subject, or endogenous HSPCs) with an effective amount of the inhibitor.

In one embodiment, the administration is by systemic route. In one embodiment, the administration is by a local route.

Source of HSPCs

HSPCs are determined suitable for hematopoietic reconstitution by the skilled practitioner, including identification of a suitable donor, appropriate collection and manipulation, prior to administration to the subject.

The HSPCs can be autologous (where the donor and recipient are the same person) and allogeneic (where the donor and recipient are different individuals). In autologous transplant, HSPCs are removed from the subject before they experience the hematopoietic damaging event (e.g., high-dose chemotherapy or radiation treatment). The cells are stored in a freezer (cryopreservation). After the damaging event, the cells are put back in the subject's body to make (regenerate) normal blood cells. This is referred to as a rescue transplant. In allogeneic transplant, HSPCs are removed from another person, referred to as a donor. Umbilical cord blood transplant is a type of allogeneic or autologous transplant depending on the source of the umbilical cord. Stem cells are removed from a newborn baby's umbilical cord right after birth. The stem cells are frozen and stored until they are needed for a transplant. Another source of donor cells is placenta.

Another source of donor cells is alternative source requiring genetic manipulation such as HSCs obtained through genetic re-programming of more mature cells or induced embryonic stem cells.

Donor HSPCs are typically collected in two ways, by bone marrow harvest or leukapheresis. Bone marrow harvest is minor surgery performed under general anesthesia, where the bone marrow is removed from the back of both hip bones. Leukapheresis is the peripheral harvest of HSPCS. The donor receives several (e.g., about 5 days) of treatments to move stem cells from the bone marrow into the blood. During leukapheresis, blood is removed from the donor through an IV line in a vein. HSPCs are separated in a machine and removed to be later given to the recipient. The red blood cells are returned to the donor.

The harvested cells are a mixture of stem cells, progenitors, and white blood cells of various degrees of maturity. The progenitor cells and/or stem cells can reconstitute all of the hematopoietic cells in a subject. These include, but are not limited to, lymphocytes, platelets, erythrocytes and myeloid cells, including, T cells, B cells (plasma cells), natural killer cells, dendritic cells, monocytes (macrophages), neutrophils, eosinophils, basophils (mast cells), megakaryocytes (platelets), and erythroblasts (erythrocytes). These cells are also capable, in addition to differentiation, of self-renewal, so as to proliferate the stem-progenitor population that is capable of differentiation.

Treatment of the Donor

Another aspect of the invention relates to treatment of a donor individual with an inhibitor of Embigin prior to donation of the HSPC for use in hematopoietic reconstitution in a subject. Hematopoietic reconstitution is achieved in a subject by administering to the recipient subject HSPC obtained from a donor subject that was previously treated with an Embigin inhibitor described herein. The treatment is to thereby induce expansion of the HSPCs in the donor prior to harvest. The induction occurs by similar mechanism as in the recipient subject. The donor is treated with the inhibitor to thereby contact the HSPCs and/or the HSPC microenvironment of the donor with an effective amount of the inhibitor. The inhibitor is administered by a route and in sufficient amount to thereby affect the HSPCs in the donor and thereby promote enhanced proliferation and expansion of those cells. In one embodiment, the inhibitor is administered by a route and in sufficient amount to thereby contact the HSPCs in the donor. As a result of the treatment, the enhanced proliferation and expansion may occur either in the donor prior to harvest, in the recipient following transplant, ex vivo, or any combination thereof. The hematopoietic reconstitution of the recipient subject is enhanced by the activity of the inhibitor in that the short term and long term reconstitution occurs faster and/or more completely (e.g, with a broader cell type populations) than otherwise would have occurred in the absence of administration of the inhibitor to the donor. In one embodiment, the donor is also treated with an inhibitor of IL-18.

Administration to the donor can be by a variety of methods, examples of which are described herein (e.g., those for the recipient). In one embodiment, the donor is also the recipient of the transplant. In one embodiment, the donor is different from the recipient of the transplant. In one embodiment, the recipient is also administered a therapeutically effective amount of an inhibitor, by the methods discussed herein.

In one embodiment, the donor has been identified or selected as a candidate for donation of HSPCs prior to administration of the inhibitor of Embigin. In one embodiment, the donor undergoes additional conditioning prior to harvest of the HSPCs. In one embodiment, the recipient undergoes additional conditioning prior to administration of the donor HSPCs.

Timing of Administration to the Donor

Administration of the inhibitor to the donor subject is prior to harvest of the HSPC. Administration may be in a single dose, or by way of multiple separate administrations over a period of time, beginning at a defined time point prior to harvest. In one embodiment, the inhibitor is administered to the subject for a period of from about 1 day to about 5 days (e.g., about 5, 4, 3, 2 or 1 days) prior to harvest of the HSPC. In one embodiment, the inhibitor is administered to the subject for a period of from about 5 days to about 10 days (e.g., about 10, 9, 8, 7, or 6 days) prior to harvest of the HSPC. In one embodiment, the inhibitor is administered to the subject for a period of from about 10 days to about 20 days (e.g., about 20, 19, 18, 17, 16, 15, 14, 13, 12, or 11 days) prior to harvest of the HSPC. In one embodiment, the inhibitor is administered to the subject for a period of from about 20 days to about 30 days (e.g., about 30, 29, 28, 27, 26, 25, 24, 23, 22, or 21 days) prior to harvest of the HSPC.

In other embodiment, in addition to administering the inhibitor described herein, the donor subject also receives granulocyte-colony stimulating factor (G-CSF) which is the standard used to stimulate more peripheral blood progenitor cells and release of hematopoietic progenitor cells from the bone marrow. In one embodiment, the G-CSF and the inhibitor described herein are administered in together in a cocktail or a composition. In other embodiments, the G-CSF and the inhibitor described herein are separate composition and administered simultaneously to the donor subject. Alternatively, the G-CSF and the inhibitor described herein are separate composition and administered sequentially to the subject.

Donor cells may be obtained from any suitable source from the donor, examples of which are described herein.

Ex Vivo Administration to the HSPC

The results presented herein also indicate that treatment of the HSPC after harvest but prior to administration (ex vivo) with the inhibitor of Embigin and/or inhibitor of IL-18 will also enhance expansion of HSPC. Such expansion is beneficial to the recipient subject and will accelerate post-transplant recovery, as described herein.

Embigin

Embigin is a transmembrane glycoprotein belonging to the immunoglobulin superfamily. Embigin is a 327 amino acid regulatory protein belonging to the immunoglobulin superfamily class of CAMs, and has two Ig-like (immunoglobulin-like) V-type domains and has several glycosylation sites (Gene ID: 133418; GenBank Accession No. NC_000005). Embigin is also a cell adhesion molecule (Guenette R S, et al. Dev Genet. 1997; 21(4):268-78; Ozawa M, et al. J Biol Chem. 1988 Mar. 5; 263(7):3059-62; Ray M E, et al. Oncogene. 1996 Jun. 20; 12(12):2527-33; Pértega-Gomes N, et al. BMC Cancer. 2011 Jul. 25; 11:312; Molinari S, et al. Mol Cell Biol. 2004 April; 24(7):2944-57). Cell adhesion molecules (CAMs) are intimately involved in a variety of cellular processes, including development, cell growth, apoptosis, and differentiation. Interaction of CAMs with components of the extracellular matrix (ECM) growth factors, and other CAMs provides an intricate regulatory mechanism for a diverse range of cellular responses. Embigin is a developmentally expressed protein that is a member of the immunoglobulin superfamily (IgSF) class of CAMs.

Inhibitors of Embigin

The term "inhibitor of Embigin" or "Embigin inhibitor" within the context of this invention refers to any molecule modulating Embigin production and/or action in such a way that Embigin production and/or activation or signaling is attenuated, reduced, or partially, substantially or completely prevented or blocked. An inhibitor of production can be any molecule negatively affecting the synthesis, processing or maturation of Embigin. The amino acid sequence and encoding nucleic acid sequence of Embigin is known in the art. Inhibitors of Embigin can be derived from the structure of the Embigin molecule, the amino acid sequence of Embigin, and also the nucleic acid sequence of Embigin. Examples of inhibitors are discussed herein.

The inhibitors considered according to the disclosure can be, for example, suppressors of gene expression of the Embigin, antisense mRNAs reducing or preventing the transcription of the Embigin mRNA or leading to degradation of the mRNA, proteins impairing correct folding, or partially or substantially preventing extracellular expression of Embigin, proteases degrading Embigin once it has been synthesized, fragments of Embigin (e.g., extracellular) or soluble versions of Embigin that interfere with Embigin binding and/or activity.

An Embigin inhibitor can be developed and verified through functional analysis by the skilled practitioner. Various assays for functional inhibition of Embigin can be used based on the discoveries reported herein. For example an observed increase in the mobilization of myeloid progenitors and colony-forming cells into the blood of a recipient following administration of the inhibitor into a subject (e.g. in an animal model system) indicates a proposed inhibitor of Embigin has activity. Similarly, observance of impaired homing and/or increased cell cycling of LKS cells pre-incubated with the inhibitor (e.g., anti-Embigin antibody) is expected and can be indicative of activity. Observance of a higher frequency and proliferative activity of primitive hematopoietic cells (e.g., as demonstrated by cell cycle and BrdU incorporation studies and an increased number of colony forming cells) in a subject treated with the inhibitor can also indicate activity. Assaying for increased proliferation of transplanted WT LKS cells in pre-treated irradiated recipients with the inhibitor is another functional assay for a suspected Embigin inhibitor.

In one embodiment, the inhibitor of Embigin is a neutralizing antibody directed against Embigin. Preparation and use of such a neutralizing antibody against Embigin is known in the art. The antibodies according to the disclosure may be polyclonal or monoclonal, chimeric, humanized, or even fully human. Recombinant antibodies and fragments thereof are characterized by high affinity binding to Embigin in vivo and low toxicity. Neutralizing antibodies are readily raised in animals such as rabbits, goat or mice by immunization with Embigin or a desired antigenic fragment thereof. Immunized mice are particularly useful for providing sources of B cells for the manufacture of hybridomas, which in turn are cultured to produce large quantities of anti-Embigin monoclonal antibodies.

In one embodiment, the antibody is G7.43.1 (Pridans et al., The Journal of Immunology, 2008, 180: 1719-1728) or a derivative thereof (e.g., humanized antibody). In one embodiment, the antibody binds the same or homologous epitope as the G7.43.1 mAb. In one embodiment, the antibody is 43G7 (Santa Cruz Biotech) or a derivative thereof (e.g., humanized antibody). In one embodiment, the antibody is C-16 (Santa Cruz Biotech) or a derivative thereof (e.g., humanized antibody). In one embodiment, the antibody is N-17 (Santa Cruz Biotech) or a derivative thereof (e.g., humanized antibody). In other embodiments, the inhibitor is any antibody fragment, (e.g., chimeric, humanized or sFv) having the variable chain of an antibody that binds the same or homologous epitope as the monoclonal antibody G7.43.1 mAb, C-16 or N-17 described above.

Monoclonal Antibodies

Monoclonal antibodies may be made using the hybridoma method first described by Kohler et al., 1975, Nature, 256:495, or may be made by recombinant DNA methods (U.S. Pat. No. 4,816,567). In the hybridoma method, a mouse or other appropriate host animal, such as a hamster or macaque monkey, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103, (Academic Press, 1986)). The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), conditions under which the growth of HGPRT-deficient cells is prevented.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOP-21 and M.C.-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, 1984, J. Immunol., 133: 3001; Brodeur et al., Monoclonal Antibody Production Techniques and Applications, pp. 51-63, Marcel Dekker, Inc., New York, (1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA). The binding affinity of the monoclonal antibody can, for example, be determined by the Scatchard analysis of Munson et al., 1980, Anal. Biochem., 107:220.

After hybridoma cells are identified that produce antibodies of the desired specificity, affinity, and/or activity, the cells may be subcloned by limiting dilution procedures and grown by standard methods (Goding, Monoclonal Antibodies: Principles and Practice, pp. 59-103 (Academic Press, 1986)). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-SEPHAROSE®, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences, Morrison, et al., 1984, Proc. Nat. Acad. Sci. U.S.A., 81:6851, or by covalently joining to the immunoglobulin coding sequence all or part of the coding sequence for a non-immunoglobulin polypeptide. In that manner, "chimeric" or "hybrid" antibodies are prepared that have the binding specificity of a neutralizing monoclonal antibody described herein.

Chimeric or hybrid antibodies also may be prepared in vitro using known methods in synthetic protein chemistry, including those involving crosslinking agents. For example, immunotoxins may be constructed using a disulfide exchange reaction or by forming a thioether bond. Examples of suitable reagents for this purpose include iminothiolate and methyl-4-mercaptobutyrimidate.

Other forms of recombinant production of antibodies known in the art may be applied to produce the inhibitory antibody.

Humanized Antibodies

Generally, a humanized antibody has one or more amino acid residues introduced into it from a non-human source. These non-human amino acid residues are often referred to as "import" residues, which are typically taken from an "import" variable domain. Humanization can be essentially performed following the method of Winter and co-workers (Jones et al., 1986, Nature, 321:522-525; Riechmann et al., 1988, Nature, 332:323-327; Verhoeyen et al., 1988, Science, 239:1534-1536), by substituting rodent CDRs or CDR sequences for the corresponding sequences of a human antibody.

Accordingly, such "humanized" antibodies are chimeric antibodies (Cabilly, supra), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

It is important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e. the analysis of residues that influence the ability of the candidate immunoglobulin to bind its antigen. In this way, FR residues can be selected and combined from the consensus and import sequence so that the desired antibody characteristic, such as increased affinity for the target antigen(s), is achieved. In general, the CDR residues are directly and most substantially involved in influencing antigen binding. For further details see U.S. Pat. Nos. 5,821,337 and 6,054,297.

Human Antibodies

Human monoclonal antibodies can be made by the hybridoma method. Human myeloma and mouse-human heteromyeloma cell lines for the production of human monoclonal antibodies have been described, for example, by Kozbor, 1984, J. Immunol. 133, 3001, and Brodeur, et al., Monoclonal Antibody Production Techniques and Applications, pages 51-63 (Marcel Dekker, Inc., New York, 1987).

It is now possible to produce transgenic animals (e.g., mice) that are capable, upon immunization, of producing a repertoire of human antibodies in the absence of endogenous immunoglobulin production. For example, it has been described that the homozygous deletion of the antibody heavy chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g. Jakobovits et al., 1993, Proc. Natl. Acad. Sci. USA 90, 2551-255; Jakobovits et al., 1993, Nature 362, 255-258.

Mendez et al. (1997, Nature Genetics 15:146-156) have further improved the technology and have generated a line of transgenic mice designated as "Xenomouse II" that, when challenged with an antigen, generates high affinity fully human antibodies. This was achieved by germ-line integration of megabase human heavy chain and light chain loci into mice with deletion into endogenous JH segment as described above. The Xenomouse II harbors 1,020 kb of human heavy chain locus containing approximately 66 VH genes, complete DH and JH regions and three different constant regions (mu, delta and chi), and also harbors 800 kb of human kappa locus containing 32 VK genes, JK segments and CK genes. The antibodies produced in these mice closely resemble that seen in humans in all respects, including gene rearrangement, assembly, and repertoire. The human antibodies are preferentially expressed over endogenous antibodies due to deletion in endogenous JH segment that prevents gene rearrangement in the murine locus.

Alternatively, phage display technology (McCafferty et al., 1990, Nature 348:552-553) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g. Johnson, Kevin S, and Chiswell, David J., 1993, Current Opinion in Structural Biology 3:564-571. Several sources of V-gene segments can be used for phage display. Clackson et al., 1991, Nature 352:624-628 isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., 1991, J. Mol Biol. 222:581-597, or Griffith et al., 1993, EMBO J. 12:725-734. In a natural immune response, antibody genes accumulate mutations at a high rate (somatic hypermutation). Some of the changes introduced will confer higher affinity, and B cells displaying high-affinity surface immunoglobulin are preferentially replicated and differentiated during subsequent antigen challenge. This natural process can be mimicked by employing the technique known as "chain shuffling" (Marks et al., 1992, BioTechnol., 10:779-783). In this method, the affinity of "primary" human antibodies obtained by phage display can be improved by sequentially replacing the heavy and light chain V region genes with repertoires of naturally occurring variants (repertoires) of V domain genes obtained from unimmunized donors. This technique allows the production of antibodies and antibody fragments with affinities in the nM range. A strategy for making very large phage antibody repertoires (also known as "the mother-of-all libraries") has been described by Waterhouse et al., 1993, Nucl Acids Res. 21:2265-2266, and the isolation of a high affinity human antibody directly from such large phage library is reported by Griffith et al., 1993, EMBO J. 12:725-734. Gene shuffling can also be used to derive human antibodies from rodent antibodies, where the human antibody has similar affinities and specificities to the starting rodent antibody. According to this method, which is also referred to as "epitope imprinting", the heavy or light chain V domain gene of rodent antibodies obtained by phage display technique is replaced with a repertoire of human V domain genes, creating rodent-human chimeras. Selection on antigen results in isolation of human variable domains capable of restoring a functional antigen-binding site, i.e. the epitope governs (imprints) the choice of partner. When the process is repeated in order to replace the remaining rodent V domain, a human antibody is obtained (see PCT patent application WO 93/06213, published 1 Apr. 1993). Unlike traditional humanization of rodent antibodies by CDR grafting, this technique provides completely human antibodies, which have no framework or CDR residues of rodent origin.

Chimeric Antibodies

Chimeric antibodies are immunoglobulin molecules characterized by two or more segments or portions derived from different animal species. Generally, the variable region of the chimeric antibody is derived from a non-human mammalian antibody, such as murine monoclonal antibody, and the immunoglobulin constant region is derived from a human immunoglobulin molecule. Preferably, both regions and the combination have low immunogenicity as routinely determined. Humanized antibodies are immunoglobulin molecules created by genetic engineering techniques in which the murine constant regions are replaced with human counterparts while retaining the murine antigen binding regions. The resulting mouse-human chimeric antibody preferably have reduced immunogenicity and improved pharmacokinetics in humans. In one embodiment, the Embigin neutralizing antibody is a humanized antibody. In one embodiment, the neutralizing antibody is fully human. Fully human antibodies and methods for their production are known in the art. The technology for producing human antibodies is described in detail e.g. in WO00/76310, WO99153049, U.S. Pat. No. 6,162,963 or AU5336100, which are incorporated by reference herein in their entirety.

Interleukin 18

In one embodiment, administration of the Embigin inhibitor is coordinated with an inhibitor of IL-18. The cytokine interleukin 18 (IL-18) was initially described as an interferon-γ (IFN-γ) inducing factor (Nakamura et al., Infect. Immun. 57, 590-595 1989). It is an early signal in the development of T-lymphocyte helper cell type 1 (TH1) responses. IL-18 acts together with IL-12, IL-2, antigens, mitogens, and possibly further factors, to induce the production of IFN-γ. IL-18 also enhances the production of GM-CSF and IL-2, potentiates anti-CD3 induced T cell proliferation, and increases Fas-mediated killing of natural killer cells. Mature IL-18 is produced from its precursor by the IL-18 converting enzyme (ICE, caspase-1).

The IL-18 receptor consists of at least two components, co-operating in ligand binding. High- and low-affinity binding sites for IL-18 were found in murine IL-12 stimulated T cells (Yoshimoto et al., 1998, J. Immunol. 161, 3400-3407), suggesting a multiple chain receptor complex. Two receptor subunits have been identified, both belonging to the IL-1 receptor family (Pamet et al., 1996, J. Biol. Chem. 271, 3967-3970; Kim et al., J. Immuno. 2001, 166, pp. 148-154). The signal transduction of IL-18 involves activation of NF-kB (DiDonato et al., 1997, Nature 388, 16514-16517). The IL-18 receptor complex consists of two receptor chains: a ligand-binding chain termed the IL-18R a chain and a signal-transducing chain termed the IL-18R β chain.

Interleukin 18 Inhibitors

The term "inhibitor of IL-18" within the context of this invention refers to any molecule modulating IL-18 production and/or action in such a way that IL-18 production and/or activation or signaling through the IL-18 Receptor is attenuated, reduced, or partially, substantially or completely prevented or blocked. An inhibitor of production can be any molecule negatively affecting the synthesis, processing or maturation of IL-18. The inhibitors considered according to the invention can be, for example, suppressors of gene expression of the interleukin IL-18, antisense mRNAs reducing or preventing the transcription of the IL-18 mRNA or leading to degradation of the mRNA, proteins impairing correct folding, or partially or substantially preventing secretion of IL-18, proteases degrading IL-18, once it has been synthesized, inhibitors of proteases cleaving pro-IL-18 in order to generate mature IL-18, such as inhibitors of caspase-1, and the like.

Examples of inhibitors of IL-18 include, without limitation, a IL-18 binding protein (IL-18BP), or an isoform, a mutein, fused protein, functional derivative, active fraction or circularly permutated derivative thereof. These isoforms, muteins, fused proteins or functional derivatives retain the biological activity of IL-18BP, in particular the binding to IL-18, and preferably have essentially at least an activity similar to IL-18BP. Ideally, such proteins have an enhanced biological activity as compared to unmodified IL-18BP. Preferred active fractions have an activity which is better than the activity of IL-18BP, or which have further advantages, like a better stability or a lower toxicity or immunogenicity, or they are easier to produce in large quantities, or easier to purify. Functional derivatives of IL-18BP may be conjugated to polymers in order to improve the properties of the protein, such as the stability, half-life, bioavailability, tolerance by the human body, or immunogenicity. To achieve this goal, IL18-BP may be linked e.g. to polyethyleneglycol (PEG). PEGylation may be carried out by known methods, described in WO 92/13095, for example.

In one embodiment, the inhibitor of IL-18 is IL-18 binding protein (IL-18BP). This is a soluble protein having a high affinity for IL-18. IL-18BP has been isolated from human urine, and the human and mouse cDNAs as well as the human gene were cloned (Novick et. al., 1999, Immunity 10, 127-136; WO 99/09063). IL-18BP is not the extracellular domain of one of the known IL18 receptors, but a secreted, naturally circulating protein. It belongs to a novel family of secreted proteins, further including several Poxvirus-encoded proteins (Novick et al., 1999). Urinary as well as recombinant IL-18BP specifically bind IL-18 with a high affinity and down modulates the biological affinity of IL-18. The IL-18BP gene was localized to the human chromosome 11q13, and no exon coding for a transmembrane domain was found in an 8.3 kb genomic sequence. Four splice variants or isoforms of IL-18BP generated by alternative mRNA splicing have been found in humans so far. They were designated IL-18BP a, b, c and d, all sharing the same N-terminus and differing in the C-terminus (Novick et al, 1999). These isoforms vary in their ability to bind IL-18. Of the four, hIL-18BP isoforms a and c are known to have the strongest neutralizing capacity for IL-18. Human IL-18BP isoform a cross-reacts with murine IL-18.

The term "IL-18 binding protein" is used herein synonymously "IL18BP" and refers to such IL-18 binding proteins as those defined in WO 99/09063 or in Novick et al., 1999, including splice variants and/or isoforms of IL-18 binding proteins, as defined in Kim et al., 2000, which bind to IL-18. In particular, human isoforms a and c of IL-18BP are useful in accordance with the present invention. The proteins useful according to the present invention may be glycosylated or non-glycosylated, they may be derived from natural sources, such as urine, or they may preferably be produced recombinantly. Recombinant expression may be carried out in prokaryotic expression systems like *E. coli*, or in eukaryotic, and preferably in mammalian, expression systems.

In one embodiment, the inhibitor is a fused protein. The term "fused protein" refers to a polypeptide comprising an IL-18BP, or a viral IL-18BP, or a mutein or fragment thereof, fused with another protein, which, e.g., has an extended residence time in body fluids. An IL-18BP or a viral IL-18BP, may thus be fused to another protein, polypeptide or the like, e.g., an immunoglobulin or a fragment thereof.

"Functional derivatives" as used herein refers to derivatives of IL-18BPs or a viral IL-18BP, and their muteins and fused proteins, which may be prepared from the functional groups which occur as side chains on the residues or the N- or C-terminal groups, by means known in the art, and are included in the invention as long as they remain pharmaceutically acceptable, i.e. they do not destroy the activity of the protein which is substantially similar to the activity of IL-18BP, or viral IL-18BPs, and do not confer toxic properties on compositions containing it. These derivatives may, for example, include polyethylene glycol side-chains, which may mask antigenic sites and extend the residence of an IL-18BP or a viral IL-18BP in body fluids. Other derivatives include aliphatic esters of the carboxyl groups, amides of the carboxyl groups by reaction with ammonia or with primary or secondary amines, N-acyl derivatives of free amino groups of the amino acid residues formed with acyl moieties (e.g. alkanoyl or carbocydic aroyl groups) or O-acyl derivatives of free hydroxyl groups (for example that of seryl or threonyl residues) formed with acyl moieties.

As "active fractions" of an IL-18BP, or a viral IL-18BP, muteins and fused proteins, the present invention covers any fragment or precursors of the polypeptide chain of the protein molecule alone or together with associated molecules or residues linked thereto, e.g., sugar or phosphate residues, or aggregates of the protein molecule or the sugar residues by themselves, provided said fraction has substantially similar activity to IL-18BP.

Administration of a combination of two or more inhibitors such as those described herein is also envisioned.

An inhibitor of IL-18 action can be an IL-18 antagonist, for example. Antagonists can either bind to or sequester the IL-18 molecule itself with sufficient affinity and specificity to partially or substantially neutralize the IL-18 or IL-18 binding site(s) responsible for IL-18 binding to the IL-18 Receptor. An antagonist may also inhibit the IL-18 signaling pathway, which is activated within the cells upon IL-18/receptor binding.

Inhibitors of IL-18 action may also be soluble IL-18 receptors or molecules mimicking the receptors, or agents blocking the IL-18 receptors, or IL-18 antibodies, such as polyclonal or monoclonal antibodies, or any other agent or molecule preventing the binding of IL-18 to its targets, thus diminishing or preventing triggering of the intra- or extracellular reactions mediated by IL-18.

In one embodiment, the inhibitor of IL-18 is an inhibitor of caspase-1 (ICE), neutralizing antibodies directed against IL-18, neutralizing antibodies directed against any of the IL-18 receptor subunits, inhibitors of the IL-18 signaling pathway, antagonists of IL-18 which compete with IL-18 and block the IL-18 receptor, and IL-18 binding proteins, isoforms, muteins, fused proteins, functional derivatives, active fractions or circularly permutated derivatives thereof inhibiting the biological activity of IL-18.

In one embodiment, the inhibitor of IL-18 is a neutralizing antibody directed against IL-18 or its receptor, IL-18R. Preparation and use of such a neutralizing antibody against IL-18 is known in the art, such as that described in U.S. Patent Publication 20040141964. Neutralizing antibodies directed to any of the IL-18R subunits, may be used in accordance with the present invention. Such neutralizing antibodies against IL-18 are known in the art, such as described in U.S. Patent Publication 20130034569. In one embodiment, the IL-18 or IL-18R neutralizing antibody is a humanized antibody. An examples of humanized anti-IL-18 antibodies is described in the European Patent Application EP 0 974 600. In one embodiment, the IL-18 neutralizing antibody is a human antibody. Another example of the inhibitor of IL-18 is an immunoglobulin fusion, i.e. the inhibitor of IL-18 is a fused protein comprising all or part of an IL-18 binding protein, which is fused to all or a portion of an immunoglobulin. Methods for making immunoglobulin fusion proteins are well known in the art, such as the ones described in WO 01/03737, for example. The person skilled in the art will understand that the resulting fusion protein of the invention retains the biological activity of IL-18BP, in particular the binding to IL-18. The fusion may be direct, or via a short linker peptide which can be as short as 1 to 3 amino acid residues in length or longer, for example, 13 to 20 amino add residues in length. Said linker may be a tripeptide of the sequence E-F-M (Glu-Phe-Met), for example, or a 13-amino add linker sequence comprising Glu-Phe-Gly-Ala-Gly-Leu-Val-Leu-Gly-Gly-Gln-Phe-Met (SEQ. ID. NO: 1) introduced between the IL-18BP sequence and the immunoglobulin sequence. The resulting fusion protein has improved properties, such as an extended residence time in body fluids (half-life), increased specific activity, increased expression level, or the purification of the fusion protein is facilitated.

IL-18BP can be fused to the constant region of an Ig molecule, such as the heavy chain regions, like the CH2 and CH3 domains of human IgG1, for example. The generation of specific fusion proteins comprising IL-18BP and a portion of an immunoglobulin are described in example 11 of WO 99/09063, for example. Other isoforms of Ig molecules are also suitable for the generation of fusion proteins according to the present invention, such as isoforms IgG2, IgG4, or other Ig classes, like IgM or IgA, for example. Fusion proteins may be monomeric or multimeric, hetero- or homo-multimeric.

Disorders for Treatment

An inhibitor of Embigin is therapeutically useful, for example, in the treatment of disorders or conditions where it is desirable to increase proliferation of bone marrow cells and their progeny, including but not limited to myeloid progenitor cells, myeloid precursor cells, neutrophils, lymphoid progenitor cells, lymphoid precursor cells, and lymphocytes. For example, subjects suffering from anemia, trauma that decreases blood cell count, chemotherapy, bone marrow transplant and radiation therapy.

For example, the Embigin inhibitor is therapeutically useful for treating conditions and disorders associated with neutropenia, lymphopenia, or immunodeficiency disorders, which may be primary or secondary immunodeficiency disorders. These conditions and disorders may be associated, for example, with genetic disorders, B cell deficiencies, T cells deficiencies, infectious diseases including bacterial and viral infection, infiltrative and hematological disorders, surgery and trauma, and administration of a therapeutic agent that has a secondary immunosuppressive effect. In some instances the secondary immunosuppressive effect results in an immunodeficiency disorder. Embigin inhibition can promote hematopoietic recovery from myelosuppression, for example, in cancer patients undergoing therapeutic treatments wherein the therapeutic agents severely lower the level of circulating leukocytes and compromise the patient's immune system. The Embigin inhibitor can be administered prior to, in combination with, or subsequent to radiation, high dose chemotherapy, or other anti-cancer drugs to promote hematopoietic recovery and/or increase the number of circulating neutrophils, B cells, and T cells.

"Neutropenia" is a condition characterized by an abnormally low number of circulating neutrophils. A patient suffering from neutropenia is at substantial risk for infection and disease, as the diminished number of neutrophils circulating in the blood substantially impairs the ability of the patient to fight any invading microorganisms. Neutropenia itself may be the result of disease, genetic disorders, drugs, toxins, and radiation as well as many therapeutic treatments, such as high dose chemotherapy (HDC) and conventional oncology therapy. For example, although many cancers have been found to be sensitive to extremely high doses of radiation or anti-neoplastic (anti-cancer) drugs, such intensive HDC is not widely used because it not only kills cancerous cells, but also frequently destroys the cells of the hematopoietic system that are responsible for generating the army of neutrophils that are necessary to maintain a functioning immune system. Complete destruction of neutrophil progenitor and precursor cells eliminates the patient's short-term capacity to generate mature neutrophils, thereby severely compromising the patient's ability to combat infection. The patient then becomes "immuno-compromised" and subject to opportunistic infection. Such a condition may ultimately result in morbidity and death. Other situations also may be encountered where there has been a severe insult to the hematopoietic system, resulting in a substantial reduction in neutrophils and precursors thereto.

Embigin neutralizing antibodies are identified based on their ability to inhibit a biological activity of Embigin, including but not limited to the promotion of adhesion to another cell or molecule, or the other functional assays described herein for identification of an Embigin inhibitor.

Accordingly, in one embodiment, provided herein is a method for increase proliferation of bone marrow cells and their progeny in vivo in a subject in need, the method comprising administering a therapeutically effective amount of an inhibitor of Embigin or a composition comprising an effective amount of an inhibitor of Embigin to the subject. In one embodiment, the subject is also administered a therapeutically effective amount of an inhibitor of IL-18 or a composition comprising an effective amount of an inhibitor of IL-18.

Pharmaceutical Compositions

Another aspect of the disclosure relates to pharmaceutical compositions comprising the inhibitor(s) of Embigin (alone or in combination with inhibitor(s) of other agents such as an inhibitor of IL-18) formulated for administration as described herein, and formulated with a pharmaceutically acceptable carrier. In one embodiment, the composition comprises the inhibitor(s) and the HSPC to be administered to a subject.

In one embodiment, provided herein is an inhibitor of Embigin, or an inhibitor of IL-18, or both for use in a method to increase proliferation of bone marrow cells and their progeny in vivo in a subject in need.

In one embodiment, provided herein is an inhibitor of Embigin, or an inhibitor of IL-18, or both for use in the manufacture of a medicament for use in a method to increase proliferation of bone marrow cells and their progeny in vivo in a subject in need.

In one embodiment, provided herein is an inhibitor of Embigin, or an inhibitor of IL-18, or both for use in a method to enhance hematopoietic reconstitution in vivo in a subject in need.

In one embodiment, provided herein is an inhibitor of Embigin, or an inhibitor of IL-18, or both for use in the manufacture of a medicament for use in a method to enhance hematopoietic reconstitution in vivo in a subject in need.

In one embodiment, provided herein is an inhibitor of Embigin, or an inhibitor of IL-18, or both for use in a method to promote hematopoiesis in vivo in a subject in need.

In one embodiment, provided herein is an inhibitor of Embigin, or an inhibitor of IL-18, or both for use in the manufacture of a medicament for use in a method to promote hematopoiesis in vivo in a subject in need.

In one embodiment, provided herein is an inhibitor of Embigin, or an inhibitor of IL-18, or both for use in a method to enhance mobilization of hematopoietic stem and progenitor cells in vivo in a donor subject so as to harvest the mobilized cells to donate to a recipient subject.

In one embodiment, provided herein is an inhibitor of Embigin, or an inhibitor of IL-18, or both for use in the manufacture of a medicament for use in a method to enhance mobilization of hematopoietic stem and progenitor cells in vivo in a donor subject so as to harvest the mobilized cells to donate to a recipient subject.

In one embodiment, provided herein is use of an inhibitor of Embigin, or an inhibitor of IL-18, or both in a method to increase proliferation of bone marrow cells and their progeny in vivo in a subject in need.

In one embodiment, provided herein is use of an inhibitor of Embigin, or an inhibitor of IL-18, or both in the manufacture of a medicament for use in a method to increase proliferation of bone marrow cells and their progeny in vivo in a subject in need.

In one embodiment, provided herein is use of an inhibitor of Embigin, or an inhibitor of IL-18, or both in a method to enhance hematopoietic reconstitution in vivo in a subject in need.

In one embodiment, provided herein is use of an inhibitor of Embigin, or an inhibitor of IL-18, or both in the manufacture of a medicament for use in a method to enhance hematopoietic reconstitution in vivo in a subject in need.

In one embodiment, provided herein is use of an inhibitor of Embigin, or an inhibitor of IL-18, or both in a method to promote hematopoiesis in vivo in a subject in need.

In one embodiment, provided herein is use of an inhibitor of Embigin, or an inhibitor of IL-18, or both in the manufacture of a medicament for use in a method to promote hematopoiesis in vivo in a subject in need.

In one embodiment, provided herein is use of an inhibitor of Embigin, or an inhibitor of IL-18, or both in a method to enhance mobilization of hematopoietic stem and progenitor cells in vivo in a donor subject so as to harvest the mobilized cells to donate to a recipient subject in need.

In one embodiment, provided herein is use of an inhibitor of Embigin, or an inhibitor of IL-18, or both in the manufacture of a medicament for use in a method enhance mobilization of hematopoietic stem and progenitor cells in vivo in a donor subject so as to harvest the mobilized cells to donate to a recipient subject in need.

In one embodiment, provided herein is a composition comprising an inhibitor of Embigin, or an inhibitor of IL-18, or both Embigin inhibitor and IL-18 inhibitor for use in a method to increase proliferation of bone marrow cells and their progeny in vivo in a subject in need.

In one embodiment, provided herein is a composition comprising an inhibitor of Embigin, or an inhibitor of IL-18, or both Embigin inhibitor and IL-18 inhibitor for use in a method to enhance hematopoietic reconstitution in vivo in a subject in need.

In one embodiment, provided herein is a composition comprising an inhibitor of Embigin, or an inhibitor of IL-18, or both Embigin inhibitor and IL-18 inhibitor for use in a method to promote hematopoiesis in vivo in a subject.

In one embodiment, provided herein is a composition comprising an inhibitor of Embigin, or an inhibitor of IL-18, or both Embigin inhibitor and IL-18 inhibitor for use in a method to enhance mobilization of hematopoietic stem and progenitor cells in vivo in a donor subject so as to harvest the mobilized cells to donate to a recipient subject.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

The pharmaceutical compositions of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle. The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means±1%.

In one respect, the present invention relates to the herein described compositions, methods, and respective component(s) thereof, as essential to the invention, yet open to the inclusion of unspecified elements, essential or not ("comprising"). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The disclosure described herein, in a preferred embodiment, does not concern a process for cloning human beings, processes for modifying the germ line genetic identity of human beings, uses of human embryos for industrial or commercial purposes or processes for modifying the genetic identity of animals which are likely to cause them suffering without any substantial medical benefit to man or animal, and also animals resulting from such processes.

The disclosure described herein, in a preferred embodiment, does not concern the destruction of a human embryo.

The present invention can be defined in any of the following numbered paragraphs:

[1] A method for enhancing hematopoietic reconstitution of a subject in need thereof comprising: a) administering to the subject hematopoietic stem/progenitor cells (HSPCs); and b) administering to the subject a therapeutically effective amount of an inhibitor of Embigin to thereby contact the administered HSPCs and/or the microenvironment of the administered HSPCs.

[2] The method of paragraph 1, wherein administering step b) is by a systemic route.

[3] The method of any one of paragraphs 1-2, wherein administering step b) is by a route selected from the group consisting of enteral and parenteral.

[4] The method of any one of paragraphs 1-3, wherein administering step b) is by intravenous administration.

[5] The method of any one of paragraphs 1-4, wherein administering step b) is performed about 8 days after administering step a).

[6] The method of any one of paragraphs 1-5, wherein the inhibitor of Embigin is administered to the subject over a period of time from about 8 days to about 100 days directly after administration of the HSPCs.

[7] The method of any one of paragraphs 1-5, wherein administering step b) is from about 8 days to about 50 days directly after administration of the HSPCs.

[8] The method of any one of paragraphs 1-5, wherein administering step b) is from about 8 days to about 28 days directly after administration of the HSPCs.

[9] The method of any one of paragraphs 6-8, wherein administering step b) is about 14 days directly after administration of the HSPCs.

[10] The method of any one of paragraphs 1-9, wherein the HSPCs are allogenic.

[11] The method of any one of paragraphs 1-9, wherein the HSPCs are autologous.

[12] The method of any one of paragraphs 1-11 wherein the HSPC are obtained from a donor subject treated with an inhibitor of Embigin and/or Interleukin 18 (IL-18) prior to harvest of the HSPCs to thereby expand the HSPCs.

[13] A method for enhancing the hematopoiesis in a subject in need thereof comprising administering to the subject a therapeutically effective amount of an inhibitor of Embigin to thereby contact hematopoietic stem/progenitor cells (HSPCs) and/or the microenvironment of the HSPCs of the subject.

[14] A method for hematopoietic stem/progenitor cells (HSPC) donation by a subject, comprising: a) administering to the subject an effective amount of an inhibitor of Embigin to thereby induce expansion of HSPCs in the donor; and b) harvesting the HSPCs from the subject.

[15] The method of paragraph 14, wherein the administering step is from a period of about 1 day to about 5 days prior to harvest of the HSPCs.

[16] The method of any one of paragraphs 13-15, further comprising administering to the subject an effective amount of an inhibitor of Interleukin 18 to thereby induce expansion of early hematopoietic progenitor cells.

[17] A method for enhanced hematopoietic reconstitution in a subject in need thereof comprising administering to the subject hematopoietic stem/progenitor cells (HSPC) obtained from a donor subject, wherein the donor subject was treated with an inhibitor of Embigin to thereby expand HSPCs prior to harvest of the HSPCs from the donor.

[18] The method of claim 17 wherein the donor subject was further treated with an inhibitor of Interleukin 18 (IL-18) to thereby expand early hematopoietic progenitor cells prior to harvest of the HSPCs from the donor

[19] The method of any one of paragraphs 17-18, wherein the donor subject is treated with the inhibitor of Embigin for a period of from about 1 day to about 10 days directly prior to harvest of the HSPCs.

[20] The method of paragraph 19, wherein the period is from about 1 day to about 5 days directly prior to harvest of the HSPCs.

[21] The method of any one of paragraphs 19-20, wherein the period is about 5 days directly prior to harvest of the HSPCs.

[22] The method of any one of paragraphs 17-21, wherein the treatment of the donor subject is by administration of the inhibitor of Embigin and/or the inhibitor of IL-18 to the donor subject by a method selected from the group consisting of enteral and parenteral.

[23] The method of any one of paragraphs 1-12, 14-22, wherein the HSPCs are obtained from bone marrow, blood, placenta, or umbilical cord of the donor.

[24] The method of any one of paragraphs 1-23, wherein the inhibitor of Embigin is selected from the group consisting of a neutralizing antibody against Embigin, a soluble form of Embigin, and a fragment of Embigin.

[25] The method of any one of paragraphs 1-24, wherein the inhibitor of Embigin is a neutralizing antibody against Embigin.

[26] The method of paragraph 25, wherein the neutralizing antibody against Embigin is a monoclonal antibody.

[27] The method of paragraph 25, wherein the antibody is a humanized antibody.

[28] The method of paragraph 25, wherein the antibody is a human antibody.

[29] The method of any one of paragraphs 1-13, further comprising administration of a therapeutically effective amount of an inhibitor of IL-18, to thereby inhibit IL-18 interaction with IL-18R molecules present on the administered HSPC.

[30] The method of any one of paragraphs 12, 13, 16, 18-29, wherein the inhibitor of IL-18 is selected from the group consisting of IL-18 binding protein, an antibody against IL-18, an antibody against an IL-18 receptor subunits, an inhibitor of the IL-18 signaling pathway, an antagonist of IL-18 which competes with IL-18 and blocks the IL-18 receptor, an inhibitor of caspase-1 (ICE), an IL-18 isoform, an IL-18 mutein, an IL-18 fused protein, an IL-18 functional derivative, an IL-18 active fraction, and an IL-18 circularly permutated derivative thereof inhibiting the biological activity of IL-18.

The invention is further illustrated by the following examples, which should not be construed as further limiting.

The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLES

Despite emerging evidence pointing to the critical role of the interaction between normal or malignant cells (1, 2) with their specialized microenvironment or "niche", the identification of markers for niche cell populations and discovery of individual niche factors remain reliant on a candidate gene approach, thus hindering our understanding of cellular interactions within the niche and development of niche-directed therapies.

The spatial proximity between a niche cell and a stem/progenitor cell governs micro-anatomic organization of niches from nematodes to mammals, including the bone marrow hematopoietic niche—the mammalian niche most extensively studied (3). Cell ablation or cell type-specific gene deletion experiments of several putative niche cell types which are spatially associated with hematopoietic stem and progenitor cells (HSPCs) resulted in quantitative and functional hematopoietic defects (4-6), suggesting that anatomical proximity between HSPCs and niche cells is essential for niche regulatory function. We therefore set out to test if proximity-based single cell analysis, i.e. transcriptome comparison between individual mesenchymal cells in the immediate proximity to transplanted HSPC and those located further away, can be used as an unbiased strategy to reveal novel niche cell subsets and regulatory molecules.

As an example of an HSPC-proximal niche cell type, we focused on the endosteum-lining osteolineage cells (OLCs) in the post-transplant bone marrow niche. OLCs regulate HSPC pool size, mobilization and quiescence (7-10) and are located in close apposition to transplanted HSPC in irradiated mice (11).

Figure 2:
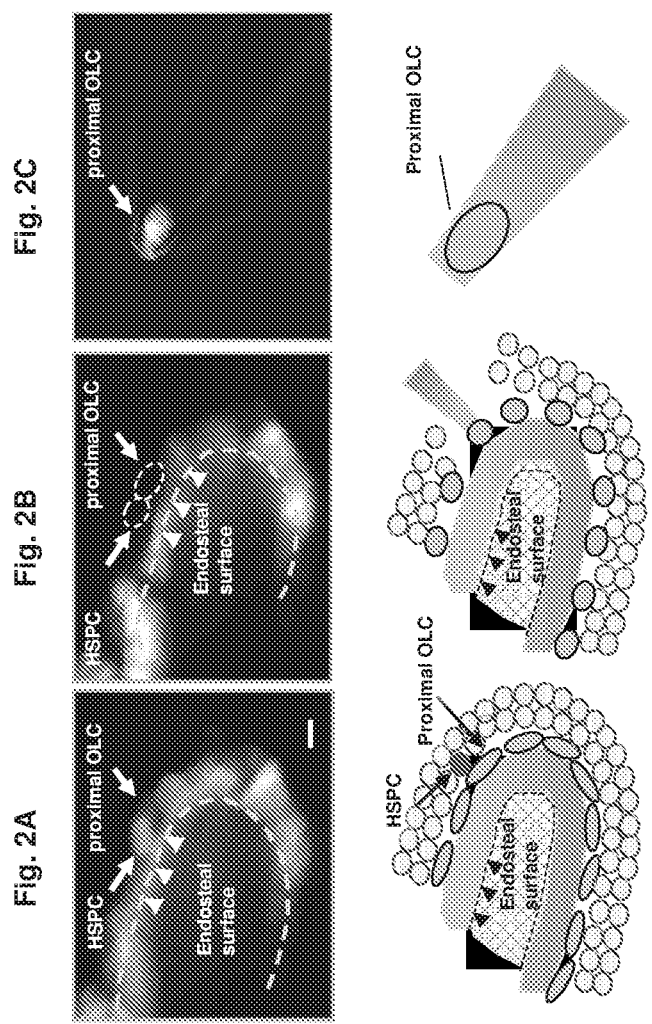
FIG. 2A-2C collectively show the experimental results that illustrates micropipette aspiration of proximal OLC. Shown are overlaid GFP and DiI images before and after retrieval of proximal OLC (top panel: microphotographs, bottom panel: corresponding schematic diagram). Scale bar: 10 μm. White indicate areas of GFP and DiI overlap.

To test our experimental approach, we transplanted irradiated newborn co12.3GFP mice (in which OLCs are GFP-positive (12)) with adult bone marrow lineage-negative (lin) $kit^+Sca1^+$ $CD34^-$ $Flk2^-$ LT-HSCs fluorescently labelled with a lipophilic membrane-bound dye, DiI (FIG. 1A). Forty-eight hours later, we detected rare OLCs harboring DiI-positive transplanted cells in their immediate proximity in trabecular bone sections from transplanted mice (FIG. 2). Using a combination of mechanical and enzymatic microdissociation, we harvested individual OLCs located within two cell diameters (proximal OLCs) and greater than five cell diameters (distal OLCs) from DiI-labeled cells and performed comparative transcriptome analysis by single cell RNA-Seq (13).

Figure 3:
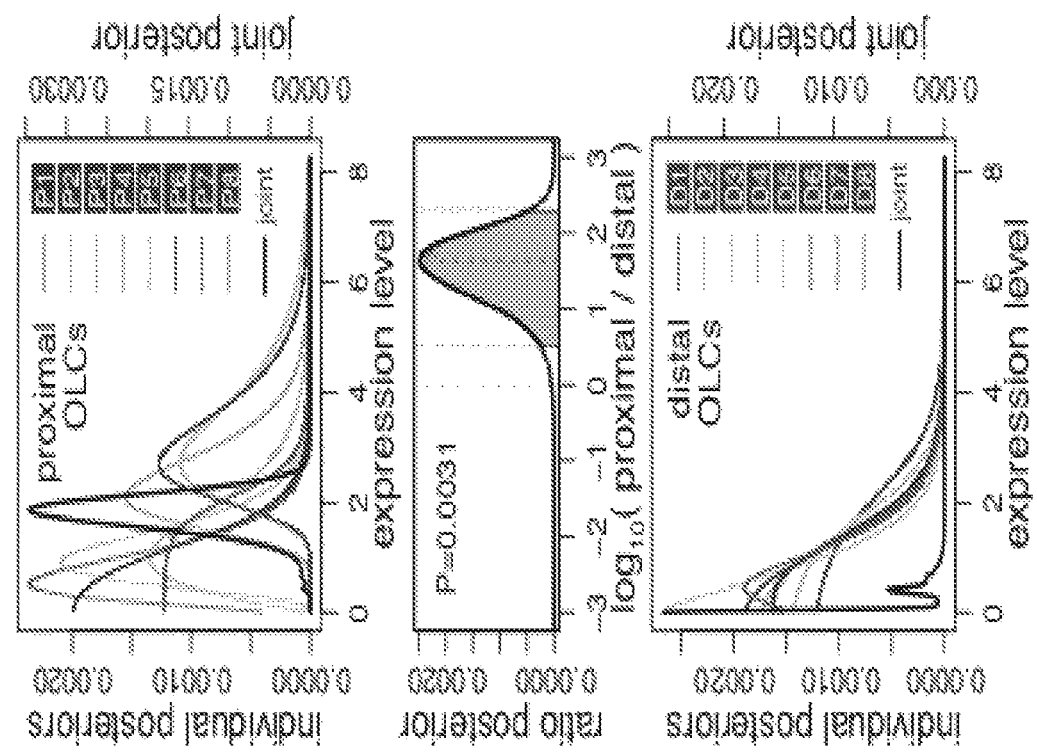
FIG. 3 shows the Bayesian approach to estimate the posterior distribution of expression levels in individual proximal and distal OLCs (different lines). The joint posteriors (black lines) describe the overall estimation of likely expression levels in each group and are used to estimate the posterior of the expression-fold difference (middle plot). The shaded area under the fold-difference posterior shows 95% confidence region. Expression of Vcam-1 gene is shown as an example.

In total, eight proximal OLCs and eight distal OLCs were examined. As expected, we observed a high degree of variability in transcript abundance, likely originating from both technical noise and intrinsic biological stochasticity. To accommodate such stochasticity, we developed a probabilistic method, which uses Bayesian approach to estimate the likelihood of expression magnitude based on the observed reads for that gene and the overall error characteristics within the transcriptome of that particular single cell sample—Single Cell Differential Expression (SCDE) (14). By comparing combined probabilistic estimates from single cell transcriptomes, the method estimated the likelihood that the level of expression of a given gene differed between proximal and distal OLCs (Vcam-1 gene shown as a representative example, FIG. 3).

Using the top 200 differentially expressed genes, we found that profiles of proximal OLCs are clustered separately from the profiles of distal OLCs (FIG. 1B). To test whether proximal and distal OLCs could be also distinguished based on a genome-wide transcriptional signature, we constructed Support Vector Machine classifiers using a set of all detected transcripts. Using a leave-two-out cross-validation strategy, we iteratively excluded pairs of proximal and distal OLCs from the training set and evaluated the ability to classify the excluded cells. The proximal and distal OLCs were correctly classified (FIG. 1C, AUC=0.854, $P<10^{-5}$). Notably, gene set enrichment analysis showed that proximal OLCs displayed a significant upregulation of genes encoding cell surface proteins (P-value $6.8\times10^{-4}$, Q-value 0.048; top genes: Vcam1, Adam9, Amot) and those involved in immune response (P-value $3.1\times10^{-6}$, Q-value 0.0090; top genes: Map3k14, Cxcl12, 1118), supporting their role in intercellular communications (FIG. 4).

Next, we analyzed expression of known niche-derived HSPC regulators (3). We discovered that with the exception of c-kit (which is mainly produced by perivascular cells (15)), proximal OLCs had significantly higher expression levels of niche-associated molecules, most notably Cxcl12 and Vcam-1 (FIG. 1D). Further, in accordance with prior studies of a regulatory OLC phenotype (10), proximal OLCs were immature, as evidenced by significantly lower levels of mature OLC markers (Spp1/osteopontin, Bglap/osteocalcin, Dmp1) but equal expression of genes of osteoblastic lineage commitment (Runx2, Sp7/osterix) (FIG. 1E). Taken together, the above data indicate that proximal OLCs possess a distinct transcriptional signature, which is indicative of their regulatory role in the HSPC niche.

Figure 6:
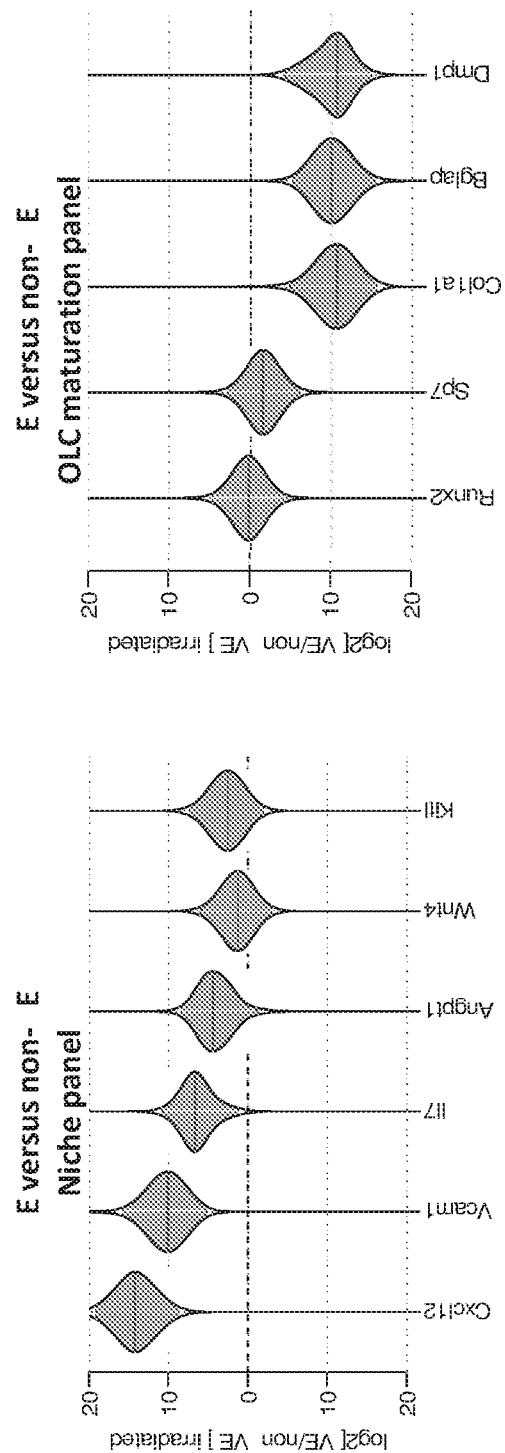
FIG. 6 shows RNA-Seq profile of niche factor and OLC maturation marker expression by VE versus non-VE cells from LT-HSC-injected adult col2.3GFP mice (n=3).

Niches are organism-wide multicellular entities and global assessment of niche function requires cell population-level approach. We asked if proximal OLC signature could be used to define cell surface markers for prospective isolation of a proximal OLC-comparable population, and whether this cell subset can respond to a change in an immediate cellular environment. We injected lethally irradiated adult col2.3GFP mice with LT-HSC, c-kit$^+$ progenitors or saline (16), and using the antibodies against VCAM-1 and Embigin (16), both of which were preferentially expressed by proximal OLCs (FIGS. 3 and 5A), isolated a rare population of col2.3GFP$^+$CD45$^-$ Ter119$^-$ VCAM-1$^+$ Embigin$^+$ cells (termed VE cells) by fluorescently-activated cell sorting (FACS). VE cells displayed immature OLC phenotype and were enriched for niche factor expression as compared to their non-VE counterparts (FIG. 6). Notably, the 200-gene signature which distinguished proximal and distal OLC (FIG. 1B), also correctly segregated VE and non-VE cells from all three experimental groups (FIG. 5C), indicating that VE cells recapitulate major transcriptional features of proximal OLCs. Interestingly, in-depth comparison of VE cell transcriptomes between the groups revealed a significant up-regulation of genes involved in cell-cell adhesion in the LT-HSC-injected group compared to the saline-injected group as assessed by gene set enrichment analysis (P-value $7.8\times10^{-5}$, Q-value 0.019, top genes Nrcam, Icam2, Esam) (FIG. 5D), suggesting that VE cells are involved in bidirectional communication within the niche: that the presence of HSPC 'shapes' the genes expressed by niche cells.

Figure 7B:
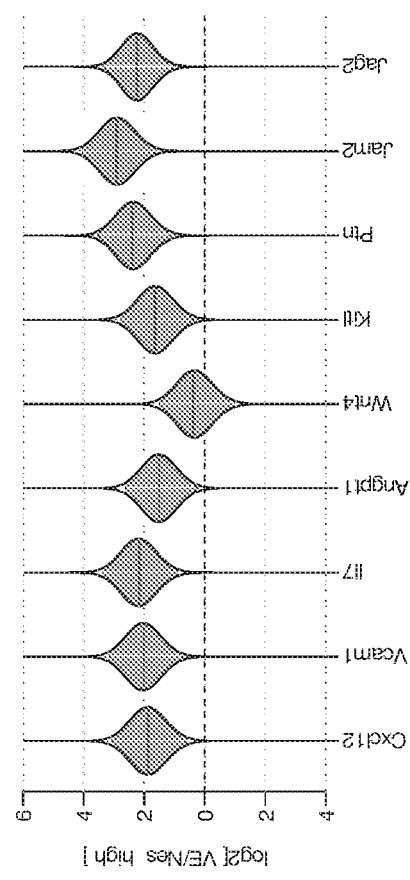
FIG. 7A-7C collectively shows experimental results that indicate sorting gates (FIG. 7A) and RNA-Seq profile of niche factor expression by VE cells versus nestin GFP-bright cells (FIG. 7B) and VE cells versus nestin GFP-dim (FIG. 7C) cells (n=3-4).
Figure 7A:
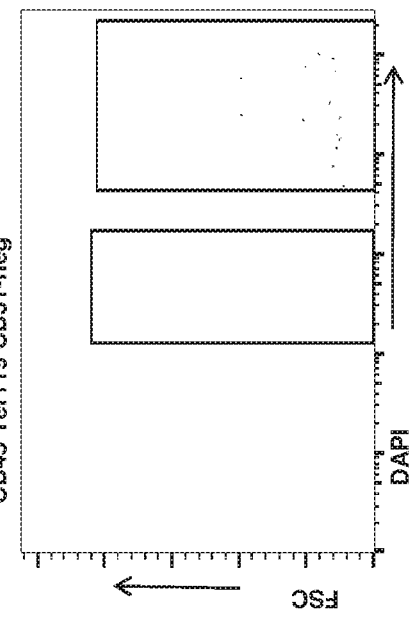

To further characterize distinct molecular properties of VE cells, we compared their niche factor expression profile with that of other known niche participants, such as nestin-GFP$^{dim}$ mesenchymal stem cells (17), nestin-GFP$^{bright}$ pericytes (4) and N-cadherin-positive osteoblastic cells (18). Given that these niche subsets were functionally defined under homeostatic conditions, we generated RNA-Seq profiles for VE cells, nestin-GFP$^{dim}$ and nestin-GFP$^{bright}$ cells from non-irradiated animals using the sorting gates as shown (FIGS. 5B and 7A). The expression data for N-cadherin+ osteoblastic cells were obtained from Dr Linheng Li, Stowers Institute.

Figure 7C:
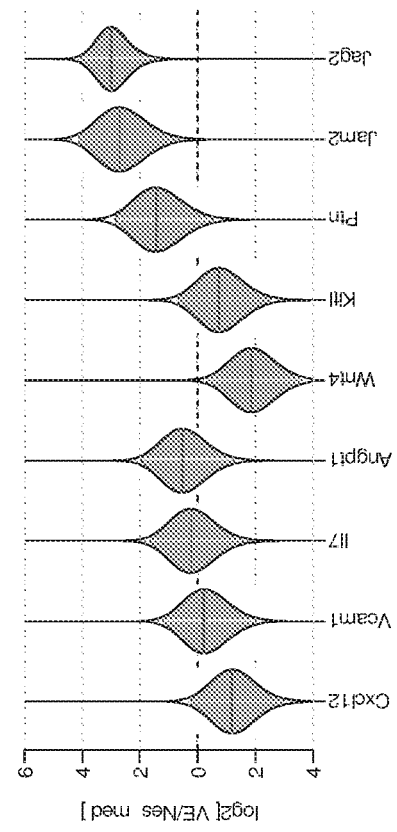

We found that in comparison with either nestin-GFP$^{dim}$ or nestin-GFP$^{bright}$ cells, VE cells had a markedly distinct expression pattern of niche-associated genes. In particular, VE cells expressed higher levels of most niche factors than nestin-GFP$^{bright}$ cells—a cell population characterized as regulating HSPC quiescence (4) (FIG. 8B). There were also clear differences between VE cells and nestin-GFP$^{dim}$ cells, with VE cells expressing higher levels of several quiescence and self-renewal mediators such as pleiotrophin (19), Jagged 2 (20) and JamB (21) (FIG. 7C). The quiescence-inducing effect of VE cells on HSPC was also evident in functional studies, which demonstrated suppression of LKS cell proliferation and corresponding lower hematopoietic colony number upon in vitro co-culture with VE cells (FIG. 5E). With regard to N-cadherin+ osteoblastic cells, flow cytometric analysis revealed that the two populations partially overlap, with approximately a third of VE cells being N-cadherin negative (FIGS. 8A and 8B). However, the two subsets were transcriptionally distinct: VE cells expressed higher levels of some quiescence-inducing factors (CXCL12, Angptl) but lower or undetectable levels of Wnt ligands, for which N-cadherin+ cells have been shown to act as the main source (18) (FIGS. 8C and 8D). Overall, the above data illustrate that VE cells are a molecularly distinct niche subset which displays HSPC quiescence-inducing properties in vitro and is able to respond to the presence of transplanted LT-HSCs in vivo.

We then investigated if the proximal OLC signature can reveal novel non-cell autonomous hematopoietic regulators in vivo. Among the transcripts for membrane-associated and secreted factors, we detected a statistically significant increase in Interleukin-18 (IL18), a pro-inflammatory cytokine (22) not previously implicated in HSPC niche function.

IL18 knock-out (IL18KO) mice displayed no apparent baseline abnormalities in the bone marrow and peripheral blood, apart from modest neutrophilia (FIG. 10). However, BrdU incorporation studies showed an increased uptake in short-term hematopoietic progenitors—short-term HSC (ST-HSC) and multi-potent progenitor (MPP) but not in LT-HSC (FIGS. 9B and 11). These changes correlated with the pattern of the IL18 receptor expression (IL18R1), which was present in short-term progenitors but almost undetectable in long-term HSCs (LT-HSCs) (FIG. 9C). Overall, these data demonstrate that IL18 regulates short-term progenitor quiescence.

Figures 13A, 13B:
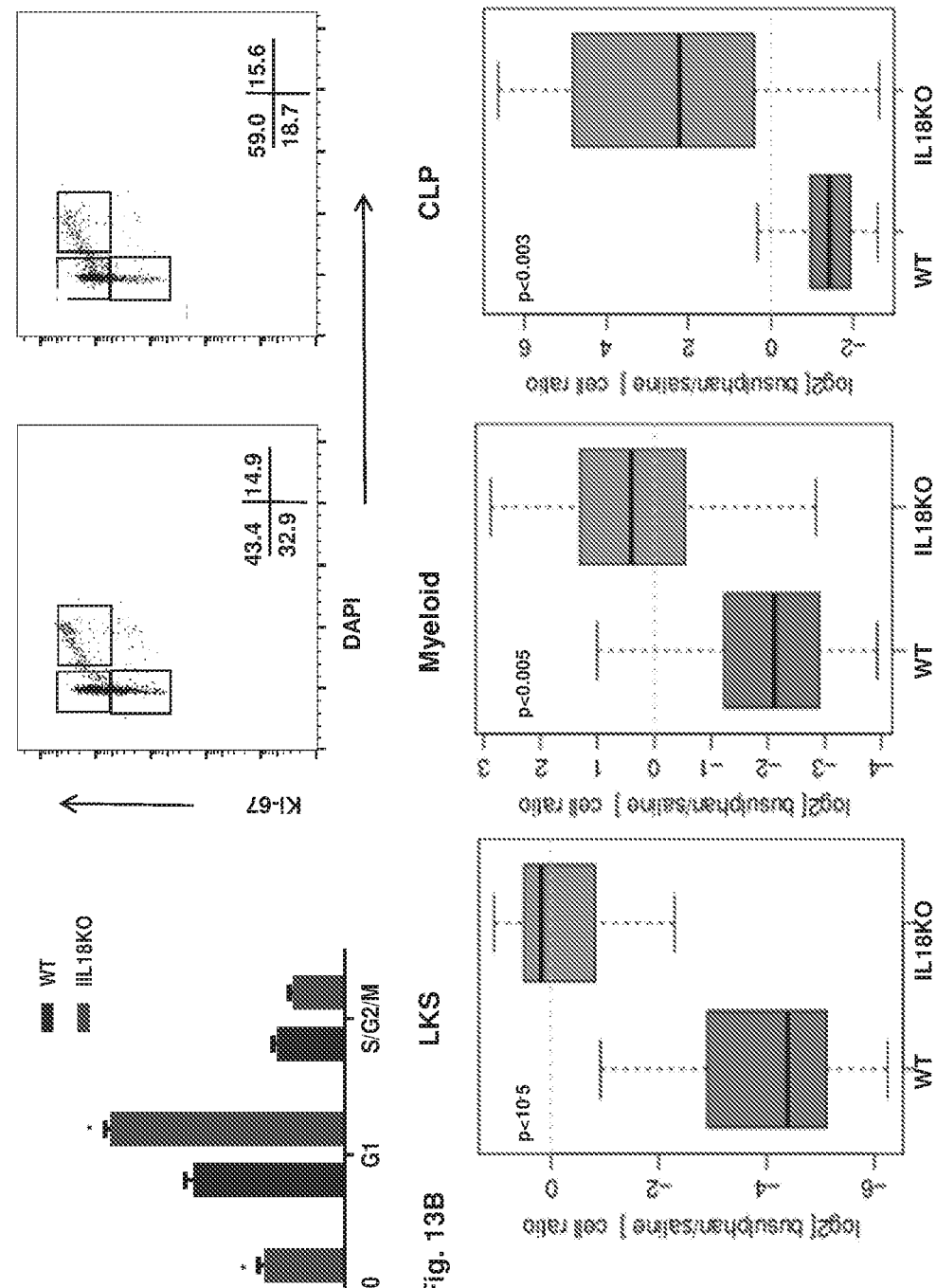
FIG. 13A-13B collectively show the assessment of HSPC proliferation and stress hematopoiesis in newborn IL18KO mice.

Functionally, short-term progenitors are critical for replenishing blood cells following bone marrow injury. Assessing progenitor cell response on day 7 post-exposure to the genotoxic agent 5-fluorouracil (5-FU) (23), we found a significantly increased frequency of lin-kit+Sca1+(LKS) cells, lin− kit+ myeloid progenitors and CLPs in IL18KO mice, as compared to 5-FU-treated wild-type (WT) controls (FIG. 9D). In contrast, exogenous administration of recombinant IL-18 protected LKS cells from 5-FU induced apoptosis, but also resulted in more sluggish hematopoietic recovery, as evidenced by a lower frequency of lineage-negative cells in rIL18-treated animals (FIGS. 9E and 12). Interestingly, loss of HSPC quiescence at baseline and exaggerated response to genotoxic injury (busulphan exposure in utero (24)) were also observed in newborn IL18KO mice (FIG. 13). In sum, these results illustrate that IL18 constrains the ability of the progenitor pool to respond to genotoxic stress and further support the role of IL18 as a regulator of progenitor quiescence.

Figure 15A:
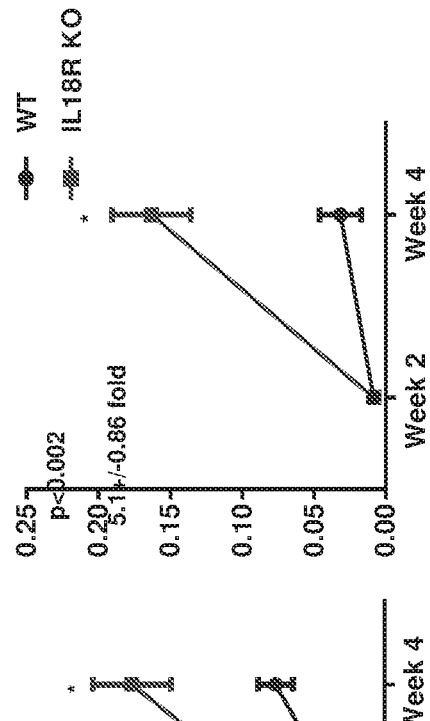
FIG. 15A-15B collectively show the assessment of short-term multi-lineage reconstitution in WT recipients of IL18R KO LKS cells.
Figure 15B:
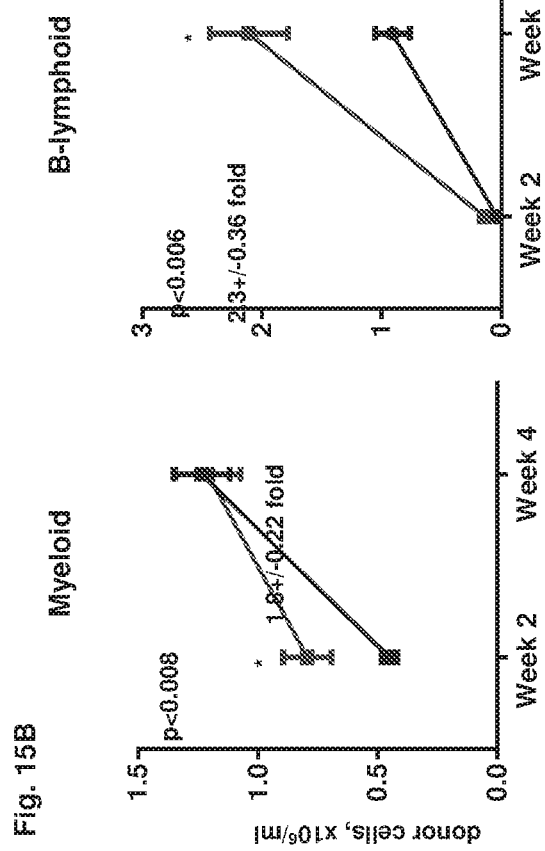
Figure 17:
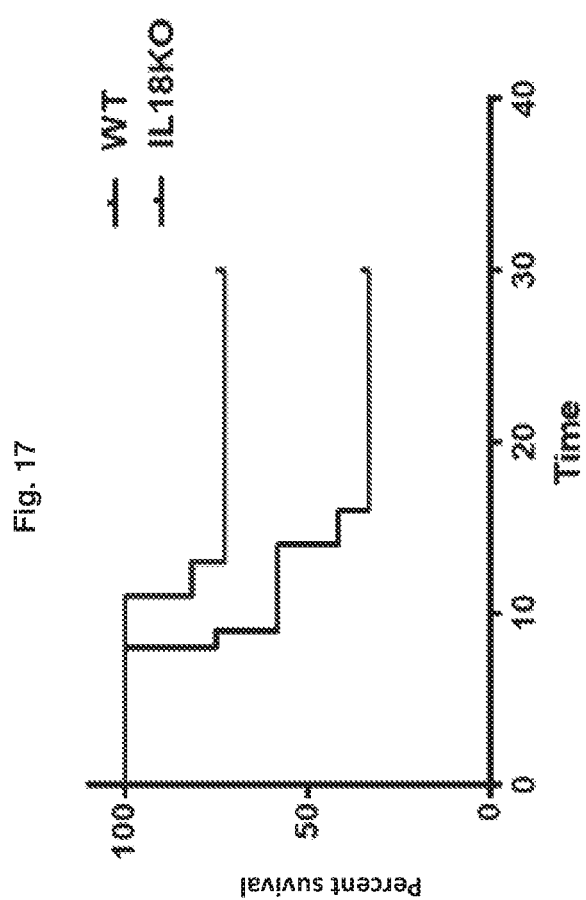
FIG. 17 shows the experimental results that indicate the survival of WT and IL18KO animals following limiting dose bone marrow transplant (10-11 per group, p=0.05)
Figure 18:
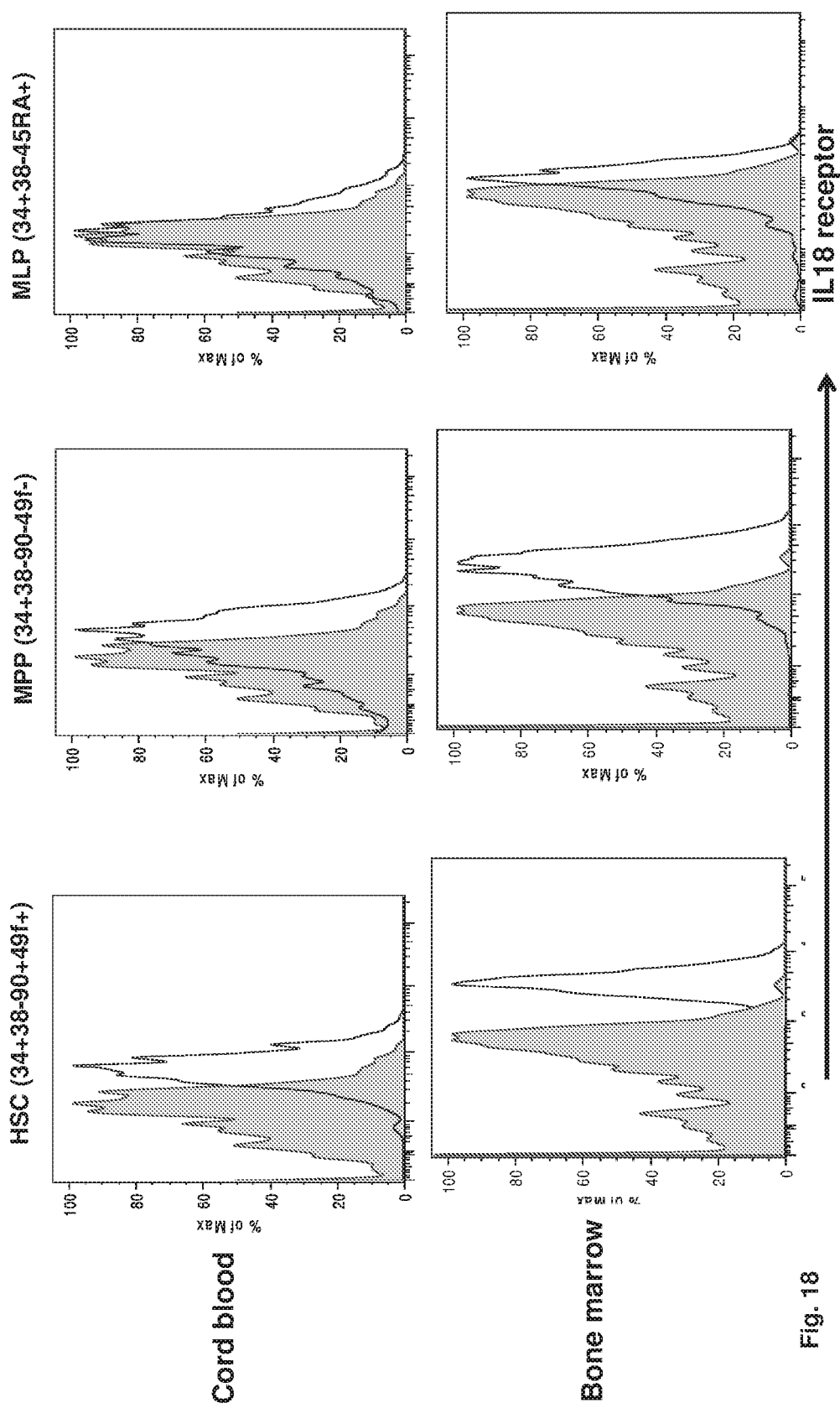
FIG. 18 shows the experimental results that indicate expression of human IL18 receptor in primitive hematopoietic cells. Representative histograms of cord blood and bone marrow analysis are shown (shaded histogram—isotype control, n=3).

To test if IL18 acts in a non-cell-autonomous fashion, we transplanted WT (CD45.1) bone marrow cells into lethally irradiated IL18KO or WT recipients (CD45.2). We found that in the IL18-deficient microenvironment, the recipient animals displayed a significantly faster short-term (up to week 4) hematopoietic reconstitution, in keeping with the absence of inhibitory effect of niche-derived IL18 on short-term progenitors (FIG. 14). Similar changes were observed upon transplantation of progenitor-enriched bone marrow fraction (LKS cells) into IL18KO hosts and accompanied by approximately 2-fold increase in both myeloid (week 2) and lymphoid (week 4) cells in peripheral blood of the recipient animals (FIG. 9F) Enhanced multi-lineage reconstitution in the absence of IL18 signaling was recapitulated in a reciprocal experiment, when sorted LKS cells from IL18 receptor knock-out animals were transplanted into WT hosts (FIG. 15), consistent with a direct effect of IL18 on progenitor proliferation. Interestingly, faster proliferation of transplanted LKS cells in IL18KO recipients was already evident at 24 hours, as shown by intra-vital imaging studies (FIG. 16), when transplanted progenitors were seen homing further away from the endosteal surface indicating that it may be explained, at least in part, by altered progenitor localization in the niche. In keeping with the above observations, we observed that the absence of IL18 in recipient mice was associated with improved survival following limiting dose transplantation (FIG. 17) raising the possibility that IL18 neutralization might be a means of reducing post-transplant cytopenias—a major cause of morbidity and mortality in patients. Given that in humans, the highest level of IL18R expression is observed in the most primitive HSPC (FIG. 18), IL18 blockade may have an additional effect on post-transplant long-term HSC expansion.

Figure 19:
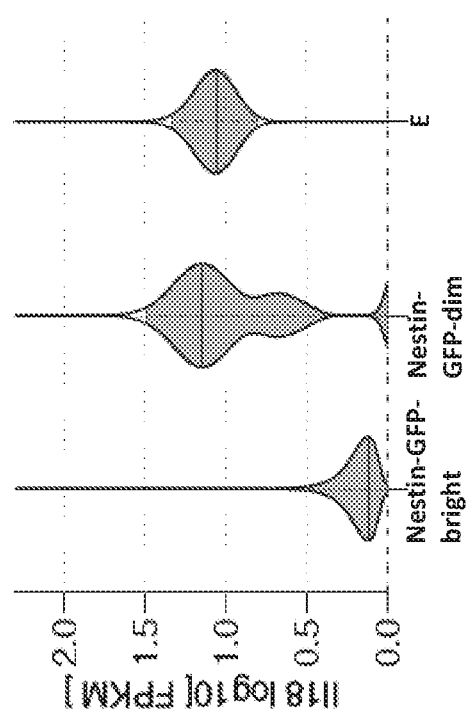
FIG. 19 shows the experimental results of RNA-Seq profile of IL18 expression in different stromal subsets. Normalized read counts (FKPM) are shown (n=3).

IL18 is expressed by multiple cell types, including perivascular cells (FIG. 19). To investigate whether IL18 production by VE cells, a proximal OLC-comparable population described above, is sufficient to induce HSPC quiescence, we co-cultured LKS cells with VE cells from WT and IL18KO animals in vitro (given that all VE cells are present within the GFP+fraction, their isolation does not require col2.3GFP reporter—FIG. 20). We found that the absence of IL18 in VE cells was associated with more robust HSPC proliferation and greater number of hematopoietic colonies (FIG. 9G, left). Importantly, IL18 deletion in non-VE cells did not affect HSPC proliferation (FIG. 9G, right), indicating that at least in vitro, VE cells were responsible for its quiescence-inducing effect.

Lastly, we checked if Embigin, a cell adhesion molecule shown here as a marker for isolation of VE cells, also has a regulatory function in the niche. Interestingly, we found that injection of neutralizing monoclonal antibody against Embigin (25) in WT mice resulted in mobilization of myeloid progenitors and colony-forming cells into the blood, suggesting a role in progenitor retention in the marrow (FIG. 21). The retention effect was accompanied by a homing defect when LKS cells were either injected into anti-Embigin pretreated animals (FIG. 21B) or pre-incubated with anti-Embigin antibody (FIG. 22). Moreover, animals treated with anti-Embigin antibody had a higher frequency and proliferative activity of primitive hematopoietic cells, as demonstrated by cell cycle and BrdU incorporation studies and an increased number of colony forming cells (FIGS. 21C and 23). Pre-treating irradiated recipients with anti-Embigin also resulted in increased proliferation of transplanted WT LKS cells, overall consistent with Embigin-mediated localization also effecting HSPC quiescence. Anti-Embigin treated animal bone marrow reconstituted poorly when competitively transplanted with untreated animal marrow into irradiated recipients (FIG. 24) likely due to the impaired homing and increased cell cycling. Collectively, these data indicate that Embigin is a previously unrecognized mediator of HSPC localization and quiescence defined through the proximity-based analytic approach.

In summary, we developed and validated a proximity-based strategy to define a distinctive subset of bone marrow mesenchymal cells that serve as a regulatory niche for HSPC. Further, through the use of this method, novel molecular mediators of HSPC quiescence and localization were identified and characterized. We found that Il18 predominantly acts on short-term progenitors while Embigin also affects LT-HSCs; however, both molecules affect cellular quiescence suggesting that the niche may not be restricted to a distinct hematopoietic cell subset, but rather regulate a specific cell state. Our results do not imply that the cells we characterized are the only source of IL18 or Embigin: these molecules, like virtually all regulators of HSPC, are expressed by other bone marrow cells. Rather, this approach can serve as a discovery vehicle for defining new candidate niche participants on both a cellular and molecular level and define the co-expression of molecules that may collectively modulate cell state. Those we identified were in the setting of irradiation and transplantation and other candidates will likely emerge when tools permitting localization of endogenous HSPC under homeostatic conditions become available. Overall, proximity-based single cell analysis may represent a widely applicable strategy to define the molecules and cell coordinating the inter-cellular communications that modulate tissue function in settings of health and disease.

Methods

Mice. Wild-type C57B16, MTMG, Sca1-GFP, Ubiquitin-GFP, IL18KO and IL18R1KO mice were obtained from the Jackson laboratory. Col2.3GFP mice were previously described (12).

Neonatal transplantation, single OLC harvesting and single cell RNA-Seq. Col2.3GFP P2 pups were irradiated 450 cGy, injected with 5000-7000 DiI (INVITROGEN®, Thermo Fisher Scientific, Waltham, Mass., USA)-labeled adult bone marrow LKS 34-Flk2– cells via anterior facial vein and sacrificed 48 hours later. Femurs were dissected, embedded in 10% low melting temperature agarose (LONZA®, Lonza Group AG, Basel, Switzerland) and sectioned at 100μ using a vibratome (LEICA®, Leica Microsystems GmbH, Wetzlar, Germany). The sections were pre-screened for the presence of rare GFP-labeled OLCs located next to single DiI-positive transplanted HSPCs, which were found in 1-2 out of 15 sections per animal.

Single OLC harvesting was performed using a physiology microscope BX51 (OLYMPUS®, Olympus Corporation, Tokyo, Japan) equipped with filters to detect GFP and DiI fluorescence, DIC optics, micromanipulators (EPPENDORFF®, Hamburg, Germany), real-time imaging camera, peristaltic pump, in-line heater, perfusion chamber (HARVARD APPARATUS®, Harvard Bioscience Inc., Holliston, Mass., USA) and SAS™ Air Syringe (RESEARCH INSTRUMENTS®, Gladbach, Germany).

The technique is based on the principle that following enzymatic digestion, the hematopoietic cells can be easily dissociated in situ, while OLCs remain partially attached to the endosteal surface thus representing a "stable target" for micropipette aspiration (Supplementary movie). Two pipettes were used in the procedure: the holding pipette (static) to secure the section in a stable stable position during perfusion, and the aspiration pipette (mobile) to perform the aspiration. The perfusion was carried out using warm (37° C.) cell dissociation solution (LIBERASE™, ROCHE HOLDING AGO, Basel Switzerland), which was continuously circulated through the perfusion chamber using a peristaltic pump (HARVARD APPARATUS®, Harvard Bioscience Inc., Holliston, Mass., USA) until a partial detachment of the target OLC from the endosteal surface was observed. Then, a positive pressure from the micromanipulator-driven PBS/BSA-filled aspiration pipette was applied to dissociate adjacent hematopoietic cells away from the target OLC. Once the target OLC became accessible, it was drawn into the aspiration pipette, the presence of GFP fluorescence was confirmed, the contents of the pipette was ejected into a PCR tube with the lysis buffer for the single cell RNA-Seq protocol, which was frozen immediately at −80° C. Reverse transcription, cDNA amplification, library preparation and SOLID® RNA-Seq (Life Technologies Corporation, Carlsbad, Calif., USA) were performed as described (13).

FACS analysis and cell sorting. Whole bone-marrow mononuclear cells (BMMNC) were collected by crushing tibias, femurs and hips and stained with the following monoclonal antibodies: c-Kit APC, CD34 FITC (E-BIOSCIENCE, INC®, San Diego, Calif., USA), Sca1 BV421, Flk2 PE, IL18Rα/CD218a (E-BIOSCIENCE, INC®), CD48 APCCy7 (BD®, Becton, Dickinson and Company, Franklin Lakes, N.J., USA), lineage cocktail biotin (B220, Mac1, Ter119, CD3, CD4, CD8 at 1:1:1:1:1:1) followed by streptavidin Pacific Orange™ (INVITROGENO) LT-HSCs, ST-HSCs and MPP were gated as described. For the lineage analysis, red cell-depleted BMMNC or peripheral blood samples were stained with CD3 APC (E-BIOSCIENCE, INC®), Mac1FITC, Gr1 PeCy7 and B220-PE (BD®). For CLP enumeration, BMMNC were stained with FITC-conjugated antibodies against Mac1, Gr1, CD19, Ter119, CD3 Pacific Blue, Flk2 PE, B220 PE Cy7 and biotin-conjugated IL7R/CD127, followed by streptavidin PerCP Cy5.5 (all from BD®). For CLP cel cycle analysis, BMMNC were stained with lineage cocktail biotin (B220, Mac1, Ter119, CD3, CD4, CD8 at 1:1:1:1:1:1) followed by PE-TEXAS RED® conjugate (INVITROGENO), B220 PE Cy5, CD127PE, Flk2APC and DAPI. For post-transplant chimerism analysis, CD45.1 AF700 and CD45.2 Pacific Blue (BD®) were added. 7-AAD (BD®) or DAPI (INVITROGEN®) were used as viability dyes. At least $2 \times 10^6$ events per sample were acquired for progenitor analysis and 104 events for lineage analysis using a BD® LSRII flow-cytometer (BD®).

For cell cycle analysis, BMMNC were stained with monoclonal antibodies for HSPC markers, as described above. The cells were permeabilized using CYTOFIX/CYTOPERM™ Fixation/Permeabilization Kit (BD®) according to the manufacturer's instructions and stained with Ki-67 FITC (BD®), Hoechst 33342 or DAPI (INVITROGENO). BrdU incorporation was assessed by BrdU administration in drinking water for 3 days, followed by flow cytometric analysis using BrdU-FITC kit (BD®, Becton, Dickinson and Company, Franklin Lakes, N.J., USA) according to manufacturer's instructions.

For FACS analysis/sorting of osteolineage cells, bone fragments were obtained by gently crushing tibiae, femora, humeri and pelvic bones of 4-6 weeks old col2.3GFP mice and mincing them with scissors. After rinsing away the bone marrow cells, the fragments were incubated with 0.25% Collagenase (STEMCELL TECHNOLOGIES®, STEMCELL Technologies, Inc., Vancouver, Canada) at 37° C. with gentle agitation for 1 hour. The samples were vortexed several times during the incubation, then filtered through 0.45 micron mesh and stained with CD45 APC Cy7, Ter 119 APC Cy7 (BD®) Embigin PE (E-BIOSCIENCE, INC.®) and CD106-APC (R&D SYSTEMS®). The samples were analysed using LSRII (BD®) or FACS-sorted using ARIA™ (BD®). Compensation and data analysis were performed using Flowjo 7.6 software. For the RNA-Seq analysis of VE and non-VE cells, lethally irradiated col2.3GFP mice were injected with 10,000 LKS CD34-Flk2-LT-HSCs, lin-kit+ Sca-progenitors or PBS and sacrificed 48 hours later. 30-50 VE cells and comparable number of non-VE cells were sorted directly into the lysis buffer (13) and frozen immediately at −80° C. Reverse transcription, cDNA amplification with 18 cycles of PCR, library preparation, SOLID®

RNA-Seq (Life Technologies Corporation, Carlsbad, Calif., USA) were performed as described for the single cell RNA-Seq samples.

VE cells from non-irradiated animals, Nestin GFPdim and Nestin GFPbright cells were isolated as described (4, 17). 150-250 cells per sample were sorted into the lysis buffer and frozen at −80° C. Reverse transcription, cDNA amplification with 12 cycles of PCR, library preparation, ILLUMINA® RNA-Seq were performed as per SMART-Seq™ protocol (ILLUMINA®, Illumina, Inc., San Diego, Calif., USA) (26) N-cadherin-positive osteoblastic cells were isolated as described (18) using biotinylated N-cadherin antibody (kindly provided by Dr Linheng Li, Stowers Institute).

For FACS analysis of IL18 receptor expression in human primitive hematopoietic cells, CD34-enriched bone marrow or cord blood cells were stained with the following antibodies: CD34APC Cy7, CD38 FITC, CD45RA APC, CD10 BV510, CD49f BV650, CD90 BV421 (all from BD®) and CD218a/IL18R1 PE (E-BIOSCIENCE, INC.®), as described (27).

Adult bone marrow/stem cell transplantation. Adult recipients (CD45.2) were irradiated 950 cGy the evening before and transplanted with 500K total bone marrow cells (CD45.1) via retro-orbital injection. For LKS cell transplantation, lethally irradiated animals were intravenously injected with 8,000 CD45.1 LKS cells and CD45.2 support cells for IL18KO experiments, 8000 CD45.2 LKS cells and CD45.2 support cells from for IL8 receptor KO experiments. Recipients' peripheral blood chimerism was assessed 2, 4, 8, 12 and 16 weeks after transplantation.

For limiting dose transplantation experiments, the animals were lethally irradiated and transplanted with 50,000 total bone marrow cells from CD45.1 donor mice. 30-day survival was recorded.

5-fluorouracil treatment. 8-12 week old age and gender matched WT or IL18KO mice were injected with 5-fluorouracil (150 mg/kg) intra-peritoneally (IP). Bone marrow was analyzed on day 8 by flow cytometry. For rIL18 pre-treatment experiments, animals were injected with 2 micrograms of recombinant mouse IL18 (R&D SYSTEMS®, Research and Diagnostic Systems, Inc., Minneapolis, Minn., USA) IP for 5 days, followed a single injection of 5FU (340 mg/kg). The animals were sacrificed at 48 hours and analyzed by flow cytometry using antibodies against c-kit, Sca-1 and lineage markers as described above and Annexin-V (BD®, Becton, Dickinson and Company, Franklin Lakes, N.J., USA) and propidium iodide for detection of apoptotic cells.

Assessment of neonatal stress hematopoiesis. Following timed matings, pregnant WT or IL18KO mothers were injected IP with 15 mg/kg busulphan in DMSO or DMSO control on day 17 and day 18 of pregnancy, as described (24). Pups were sacrificed on the day of birth, the bone marrow was isolated by gentle crushing of the skeleton and analyzed using cell surface markers as described above in combination with CD45 in order to exclude contaminating non-hematopoietic cells.

Co-culture experiments. These were performed as described (28, 29) with some modifications. VE and non-VE cells were isolated from 4-week old WT or IL18KO animals, plated in collagen-coated 384-well plates (CORNING®, Corning, Inc. Corning, N.Y., USA) at the density of 4000 cell per well in BMMSC media (LONZA®, Lonza Group AG, Basel, Switzerland) and cultured overnight. The following day, 1000 LKS cells sorted from Ubiquitin-GFP mice were added and the media was supplemented with the following cytokines and growth factors (PEPROTECH®, Peprotech, Inc. Rocky Hill, N.J., USA): murine stem cell factor and interleukin-3 (10 ng/mL), insulin-like growth factor 1 and thrombopoietin (20 ng/mL), interleukin-6 and Fms-like tyrosine kinase 3 (25 ng/mL). HSPC number was assessed daily by quantifying the number of GFP+ cells per well with ImageJ software. On day 3, the content of each well was trypsinized and split between 3 technical replicates for CFC assay in METHOCULT™ 3434 (STEMCELL TECHNOLOGIES®, STEMCELL Technologies, Inc., Vancouver, Canada).

Bioinformatics and statistical analysis. The differential expression estimates were obtained from single-cell RNA-seq data using the approach described (14). The stability of differential expression signature distinguishing OLC-proximal and distal cells was tested using support vector machine (SVM) classifier as follows: the SVM classifiers were constructed using all genes for which expression was detected in any of the examined cells; the ability to distinguish OLC-proximal and distal cells was tested using leave-two-out validation: one OLC-proximal and one OLC-distal cell was excluded, and a v-classification SVM was constructed based on all remaining cells using e 1071 R package. All possible pairs of OLC-proximal and distal cells were tested to evaluate the classification performance (FIG. 2C). Gene set enrichment analysis (GSEA) was performed using mouse GO annotations from Mouse Genome Database (2013 Dec. 27 version, available on the world wide web at http://<www.informatics.jax.org/≥ for gene listings). A total of 1590 GO categories (BP or CC) containing between 10 and 2000 genes were tested, taking into account the magnitude of the expression differences. In the analysis of the single-cell differential expression, the mode of the log-fold expression difference posterior distributions was used as a difference magnitude (with power factor p=0.5). The empirical P-values were determined based on 106 randomizations, with Q-values derived using Benjamini & Hochberg correction. RNA-Seq data from bulk-sorted samples was aligned to the NCBI mm9 annotation (61) using TopHat. The expression fold-differences were estimated using HTSeq and DESeq. The GSEA was performed using signed expression difference Z-score (power factor p=2, 106 randomizations). To verify classification of the bulk samples based on the 200-gene signature (FIG. 2C), RPKM estimates were used, correcting for mouse batch effect using ComBat (30). The classification was calculated using Ward method hierarchical clustering, with a Euclidean distance metric. The single cell and bulk analysis RNA-Seq data has been deposited in GEO under accession number GSE52359.

Intravital microscopy. WT C57B16 mice or IL18KO mice were irradiated 950 cGy the night before and intravenously injected with 50,000 LKS cells obtained from MTMG mice or ScaGFP mice to enable fluorescent HSPC labeling. Intravital imaging of calvarial bone marrow and data analysis were performed at 24 hours and 48 hours post-transplant, as previously described (11). Doubling rate was calculated using the following formula: Tr=log 2 (N48/N24) where Tr is the doubling rate and N48 and N24 are cell numbers per calvarial bone marrow at 48 and 24 hours post-injection.

Anti-Embigin experiments. For all experiments, we used a neutralizing antibody against Embigin (clone G7.43.1; E-BIOSCIENCE, INC.® and a gift from Dr S Nutt) and IgG2b control antibody (E-BIOSCIENCE, INC.®), which were injected either intravenously or IP at 2 mg/kg/day. For Embigin mobilization experiments, mice were injected with anti-Embigin antibody and isotype control for 3 days. Twenty-four hours after the last injection, peripheral blood was collected via cardiac puncture and phenotypic progenitors determined by flow cytometry and functional progenitors determined by colony assays in methylcellulose as previously described (31). For the homing experiments, 50,000 LKS cells from Scal-GFP mice were incubated with anti-Embigin or isotype control antibody at 10 microgram/ml for 30 minutes on ice prior to injection into lethally irradiated WT C57B6 recipients. Alternatively, WT recipient mice were treated with anti-Embigin or isotype control antibody at 2 mg/kg/day for 3 days, lethally irradiated and injected with 50,000 freshly sorted LKS cells from Scal-GFP mice. 24 and 48 hours later, the number of cells which homed to calvarial bone marrow was quantified by intravital microscopy. For HSPC subset quantification, cell cycle studies, BrdU incorporation experiments, colony assays and competitive transplants, WT animals were injected with anti-Embigin antibody and isotype control for 3 days at 2 mg/kg/day. For competitive transplant, recipient SJL (CD45.1) mice were lethally irradiated and transplanted 500,000 bone marrow cells from anti-Embigin or isotype control-treated C57B16 mice and 500,000 bone marrow competitor cells from CD45.1 mice.

REFERENCES

1. A. Mendelson, P. S. Frenette, Hematopoietic stem cell niche maintenance during homeostasis and regeneration. Nature medicine 20, 833 (August, 2014).
2. M. A. Swartz et al., Tumor microenvironment complexity: emerging roles in cancer therapy. Cancer Res 72, 2473 (May 15, 2012).
3. S. J. Morrison, D. T. Scadden, The bone marrow niche for haematopoietic stem cells. Nature 505, 327 (Jan. 16, 2014).
4. Y. Kunisaki et al., Arteriolar niches maintain haematopoietic stem cell quiescence. Nature 502, 637 (Oct. 31, 2013).
5. L. Ding, T. L. Saunders, G. Enikolopov, S. J. Morrison, Endothelial and perivascular cells maintain haematopoietic stem cells. Nature 481, 457 (Jan. 26, 2012).
6. A. Greenbaum et al., CXCL12 in early mesenchymal progenitors is required for haematopoietic stem-cell maintenance. Nature 495, 227 (Mar. 14, 2013).
7. L. M. Calvi et al., Osteoblastic cells regulate the haematopoietic stem cell niche. Nature 425, 841 (Oct. 23, 2003).
8. F. Ferraro et al., Diabetes impairs hematopoietic stem cell mobilization by altering niche function. Sci Transl Med 3, 104ra101 (Oct. 12, 2011).
9. F. Arai et al., Tie2/angiopoietin-1 signaling regulates hematopoietic stem cell quiescence in the bone marrow niche. Cell 118, 149 (Jul. 23, 2004).
10. M. H. Raaijmakers et al., Bone progenitor dysfunction induces myelodysplasia and secondary leukaemia. Nature 464, 852 (Apr. 8, 2010).
11. C. Lo Celso et al., Live-animal tracking of individual haematopoietic stem/progenitor cells in their niche. Nature 457, 92 (Jan. 1, 2009).
12. Z. Kalajzic et al., Directing the expression of a green fluorescent protein transgene in differentiated osteoblasts: comparison between rat type I collagen and rat osteocalcin promoters. Bone 31, 654 (December, 2002).
13. F. Tang et al., mRNA-Seq whole-transcriptome analysis of a single cell. Nat Methods 6, 377 (May, 2009).
14. P. Kharchenko, L. Silberstein, D. T. Scadden, Bayseian approach to single cell differential expression analysis. Nature Methods, (2014).
15. L. Ding, S. J. Morrison, Haematopoietic stem cells and early lymphoid progenitors occupy distinct bone marrow niches. Nature 495, 231 (Mar. 14, 2013).
16. R. P. Huang, M. Ozawa, K. Kadomatsu, T. Muramatsu, Developmentally regulated expression of embigin, a member of the immunoglobulin superfamily found in embryonal carcinoma cells. Differentiation 45, 76 (November, 1990).
17. S. Mendez-Ferrer et al., Mesenchymal and haematopoietic stem cells form a unique bone marrow niche. Nature 466, 829 (Aug. 12, 2010).
18. R. Sugimura et al., Noncanonical Wnt signaling maintains hematopoietic stem cells in the niche. Cell 150, 351 (Jul. 20, 2012).
19. H. A. Himburg et al., Pleiotrophin mediates hematopoietic regeneration via activation of RAS. The Journal of clinical investigation 124, 4753 (November, 2014).
20. J. M. Butler et al., Endothelial cells are essential for the self-renewal and repopulation of Notch-dependent hematopoietic stem cells. Cell Stem Cell 6, 251 (March 5).
21. M. L. Arcangeli et al., JAM-B regulates maintenance of hematopoietic stem cells in the bone marrow. Blood 118, 4609 (Oct. 27, 2011).
22. H. Okamura et al., Cloning of a new cytokine that induces IFN-gamma production by T cells. Nature 378, 88 (Nov. 2, 1995).
23. H. E. Broxmeyer et al., Dipeptidylpeptidase 4 negatively regulates colony-stimulating factor activity and stress hematopoiesis. Nature medicine 18, 1786 (December, 2012).
24. E. M. Bruscia et al., Engraftment of donor-derived epithelial cells in multiple organs following bone marrow transplantation into newborn mice. Stem cells 24, 2299 (October, 2006).
25. C. Pridans et al., Identification of Pax5 target genes in early B cell differentiation. Journal of immunology 180, 1719 (Feb. 1, 2008).
26. J. J. Trombetta et al., Preparation of Single-Cell RNA-Seq Libraries for Next Generation Sequencing. Current protocols in molecular biology/edited by Frederick M. Ausubel [et al.] 107, 4 22 1 (2014).
27. F. Notta et al., Isolation of single human hematopoietic stem cells capable of long-term multilineage engraftment. Science 333, 218 (Jul. 8, 2011).
28. Y. Nakamura et al., Isolation and characterization of endosteal niche cell populations that regulate hematopoietic stem cells. Blood 116, 1422 (Sep. 2, 2010).
29. B. R. Chitteti et al., Impact of interactions of cellular components of the bone marrow microenvironment on hematopoietic stem and progenitor cell function. Blood 115, 3239 (Apr. 22, 2010).
30. W. E. Johnson, C. Li, A. Rabinovic, Adjusting batch effects in microarray expression data using empirical Bayes methods. Biostatistics 8, 118 (January, 2007).
31. J. Hoggatt et al., Differential stem- and progenitor-cell trafficking by prostaglandin E2. Nature 495, 365 (Mar. 21, 2013).

What is claimed:
1. A method for enhancing hematopoietic reconstitution in a subject in need thereof, the method comprising:
  a) administering to the subject a composition comprising hematopoietic stem/progenitor cells (HSPCs); and
  b) administering to the subject a therapeutically effective amount of an antibody that binds to Embigin and inhibits or reduces the expression or activity of Embigin on the surface of the HSPCs wherein the therapeutically effective amount of the antibody increases the level of re-populating neutrophils and lymphocytes in the subject by at least 10% as compared to the level of re-populating neutrophils and lymphocytes in a subject that has not received the antibody that binds to Embigin.

2. The method of claim 1, wherein administering step b) is by a systemic route.

3. The method of claim 2, wherein administering step b) is by a route selected from the group consisting of enteral and parenteral.

4. The method of claim 2, wherein administering step b) is by intravenous administration.

5. The method of claim 1, wherein administering step b) is performed about 8 days after administering step a).

6. The method of claim 1, wherein the antibody that binds to Embigin is administered to the subject over a period of time selected from the group consisting of: from about 8 days to about 50 days directly after administration of the HSPCs, from about 8 days to about 28 days directly after administration of the HSPCs, from about 8 days to about 100 days directly after administration of the HSPCs, and about 14 days directly after administration of the HSPCs.

7. The method of claim 1, wherein the HSPCs are allogenic.

8. The method of claim 1, wherein the HSPCs are autologous.

9. The method of claim 1, wherein the HSPCs are obtained from a donor subject, and wherein the subject is treated with an inhibitor of Embigin and/or an inhibitor of Interleukin 18 (IL-18) prior to harvest of the HSPCs to thereby expand the HSPCs.

10. The method of claim 1, wherein the HSPCs are obtained from bone marrow, blood, placenta, or umbilical cord of a donor subject.

11. The method of claim 1, wherein the antibody that binds to Embigin is selected from the group consisting of: a neutralizing antibody against Embigin, a monoclonal antibody against Embigin, a humanized antibody against Embigin, and a human antibody against Embigin.

12. The method of claim 1, further comprising a step of administering to the subject an effective amount of an inhibitor of interleukin 18 (IL-18), wherein the inhibitor of IL-18 inhibits IL-18 interaction with an interleukin 18 receptor (IL-18R) molecule present on the administered HSPCs.

13. The method of claim 12, wherein the inhibitor of IL-18 is selected from the group consisting of: an IL-18 binding protein, an antibody against IL-18, an antibody against an IL-18 receptor subunit, an inhibitor of the IL-18 signaling pathway, an antagonist of IL-18 which competes with IL-18 and blocks the IL-18 receptor, inhibiting the biological activity of IL-18, and combinations thereof.

14. The method of claim 9, wherein the inhibitor of IL-18 is selected from the group consisting of: an IL-18 binding protein, an antibody against IL-18, an antibody against an IL-18 receptor subunit, an inhibitor of the IL-18 signaling pathway, an antagonist of IL-18 which competes with IL-18 and blocks the IL-18 receptor, inhibiting the biological activity of IL-18, and combinations thereof.

* * * * *